(12) United States Patent
Choi et al.

(10) Patent No.: US 12,055,544 B2
(45) Date of Patent: Aug. 6, 2024

(54) DIAGNOSTIC ASSAY DEVICE HAVING MICROREACTOR

(71) Applicant: Access Bio, Inc., Somerset, NJ (US)

(72) Inventors: Young Ho Choi, Belle Mead, NJ (US); Jungho Back, Woodside, NY (US); Hyoungsoo Kim, New Brunswick, NJ (US); Hanmaru Chon, East Brunswick, NJ (US); Myungkyu Jang, Daegu (KR); Hyeon Suk Kim, Dayton, NJ (US); Myoun Woo Kim, Somerset, NJ (US); Hyewon Park, Somerset, NJ (US); Suji Lee, Cherry Hill, NJ (US); Olivia Haejeong Kim, Somerset, NJ (US)

(73) Assignee: Access Bio, Inc., Somerset, NJ (US)

( * ) Notice: Subject to any disclaimer, the term of this patent is extended or adjusted under 35 U.S.C. 154(b) by 0 days.

(21) Appl. No.: 18/455,410

(22) Filed: Aug. 24, 2023

(65) Prior Publication Data

US 2024/0069016 A1 Feb. 29, 2024

Related U.S. Application Data

(60) Provisional application No. 63/373,531, filed on Aug. 25, 2022.

(51) Int. Cl.
*G01N 33/543* (2006.01)
*B01J 19/00* (2006.01)
(Continued)

(52) U.S. Cl.
CPC .... *G01N 33/54391* (2021.08); *B01J 19/0093* (2013.01); *B01L 3/5029* (2013.01);
(Continued)

(58) Field of Classification Search
CPC ................. B01L 3/5029; B01L 3/5023; B01L 2300/0825; B01L 2300/0861;
(Continued)

(56) References Cited

U.S. PATENT DOCUMENTS

| 4,741,346 A | 5/1988 | Wong et al. |
| 4,912,034 A | 3/1990 | Kalra et al. |

(Continued)

OTHER PUBLICATIONS

Invitation to Pay Additional Fees and, Where Applicable, Protest Fee dated Nov. 24, 2023 in International Application No. PCT/US2023/030900 in 4 pages.
(Continued)

*Primary Examiner* — Jill A Warden
*Assistant Examiner* — Dwayne K Handy
(74) *Attorney, Agent, or Firm* — Knobbe, Martens, Olson & Bear, LLP

(57) ABSTRACT

Diagnostic assay devices for detecting the presence of an analyte in a sample solution may comprise a microreactor configured to form a sample solution containing the analyte, flow the sample solution therethrough in a first direction to form an analyte-capture molecule complex, and transfer the sample solution to an absorbent strip pad configured to flow
(Continued)

therethrough, in a second direction crossing the first direction, the sample solution including the analyte-capture molecule complex and indicate a presence of the analyte-capture molecule complex. The diagnostic devices may be used, for example, to identify the presence of SARS-Cov2, RSV, influenza A, influenza B or other pathogens in samples from patients.

27 Claims, 17 Drawing Sheets

(51) Int. Cl.
    *B01L 3/00*           (2006.01)
    *G01N 33/569*      (2006.01)

(52) U.S. Cl.
    CPC .......... *B01L 3/56* (2013.01); *G01N 33/54387* (2021.08); *G01N 33/54389* (2021.08); *G01N 33/56983* (2013.01); *B01L 2200/0668* (2013.01); *B01L 2300/0609* (2013.01); *B01L 2300/0681* (2013.01); *B01L 2300/069* (2013.01); *B01L 2300/0809* (2013.01); *B01L 2300/0825* (2013.01); *G01N 2333/08* (2013.01); *G01N 2333/165* (2013.01); *G01N 2469/10* (2013.01)

(58) Field of Classification Search
    CPC ....... G01N 33/54387; G01N 33/54388; G01N 33/54389
    See application file for complete search history.

(56) References Cited

U.S. PATENT DOCUMENTS

| | | | |
|---|---|---|---|
| 4,943,522 A * | 7/1990 | Eisinger | ........... G01N 33/54386 436/514 |
| 5,016,644 A | 5/1991 | Guirguis | |
| 5,022,411 A | 6/1991 | Guirguis | |
| 5,160,701 A | 11/1992 | Brown, III et al. | |
| 5,215,102 A | 6/1993 | Guirguis | |
| 5,559,041 A | 9/1996 | Kang et al. | |
| 2002/0085958 A1 | 7/2002 | Nemcek et al. | |
| 2010/0081214 A1 | 4/2010 | Choi et al. | |
| 2017/0227536 A1* | 8/2017 | Matsuura | ............. G01N 1/4055 |
| 2021/0389316 A1 | 12/2021 | Egan et al. | |

OTHER PUBLICATIONS

Ellume COVID-19 Home Test—Product Information Leaflet, Ellume Limited, 2 pages, Mar. 2022.
Huang et al., "Disposable Autonomous Device for Swab-to-Result Diagnosis of Influenza," Anal. Chem., vol. 89, pp. 5776-5783, 2017.
International Search Report and Written Opinion dated Jan. 30, 2024 in Application No. PCT/US2023/030900 in 23 pages.

\* cited by examiner

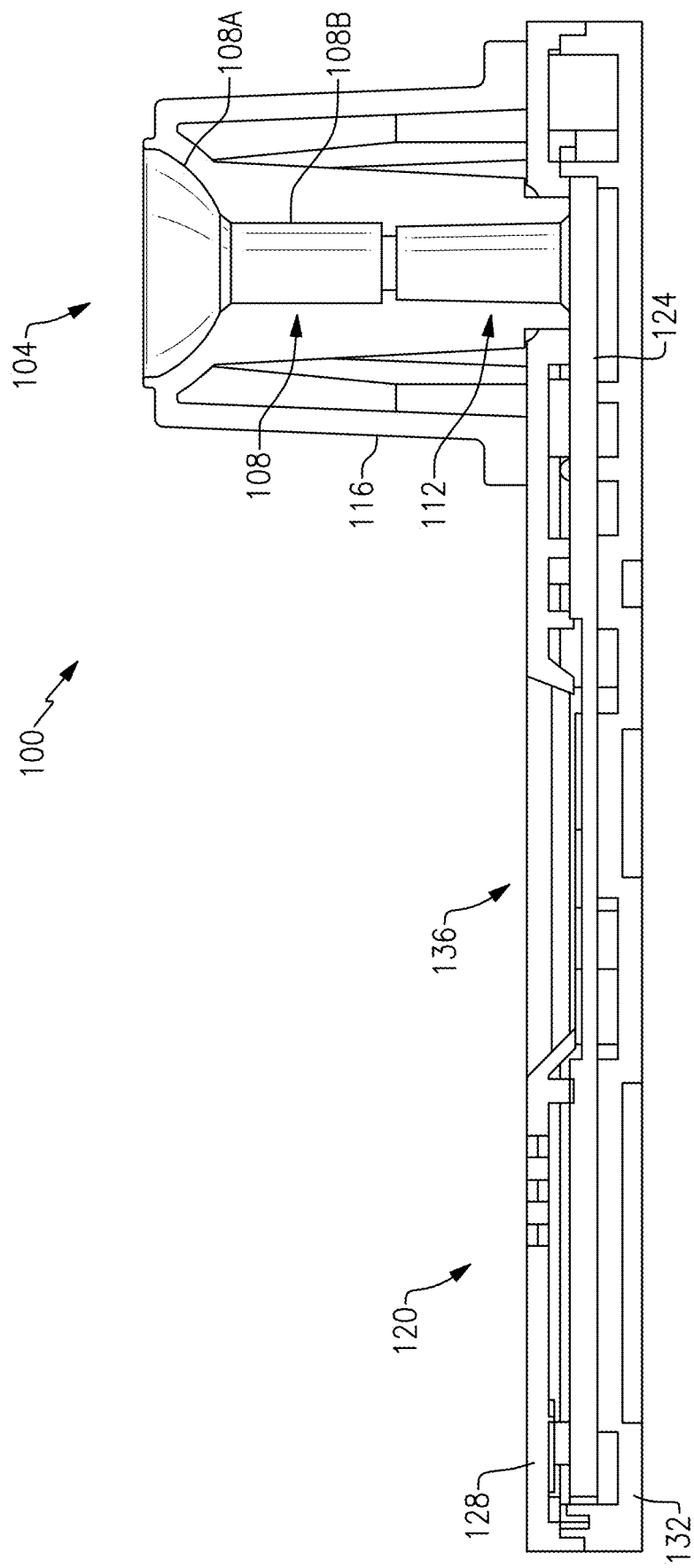

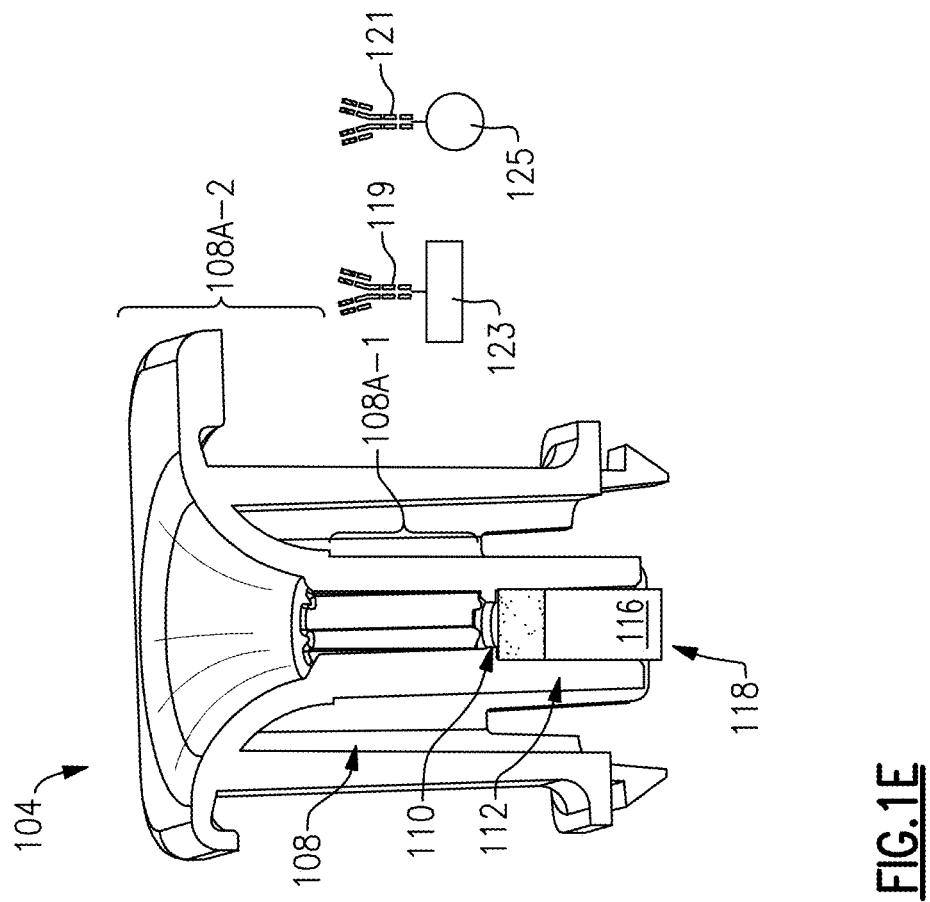
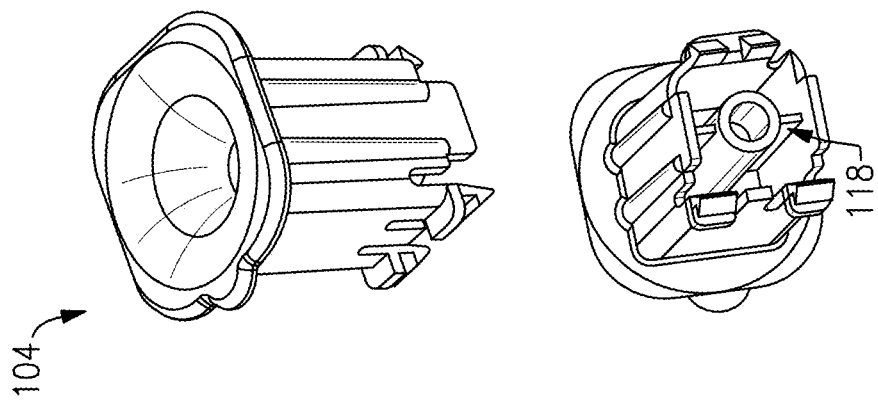
FIG.1E

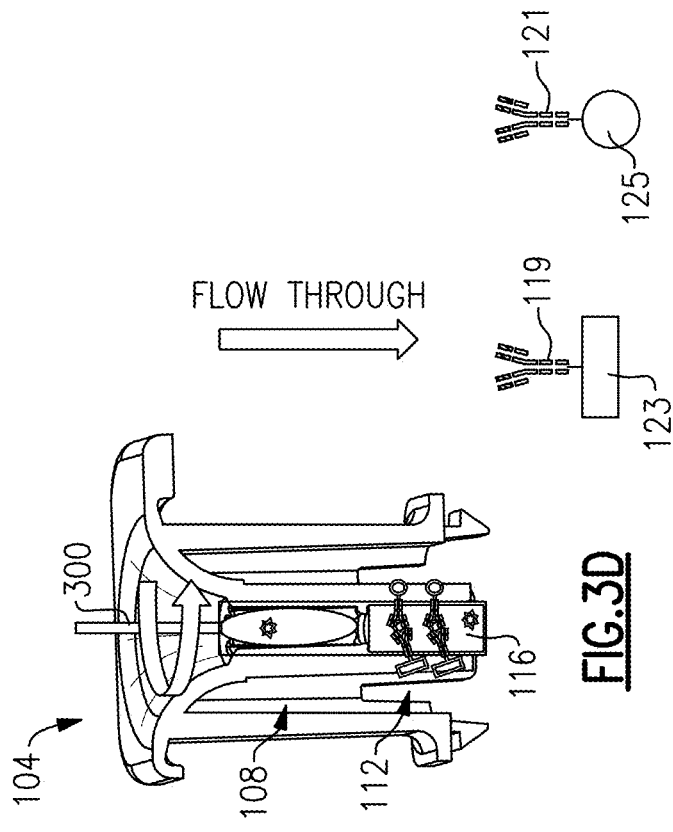
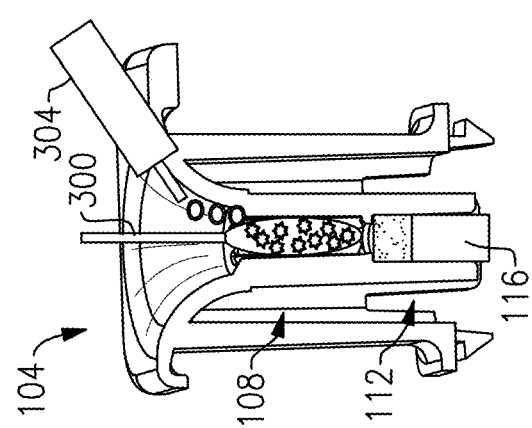
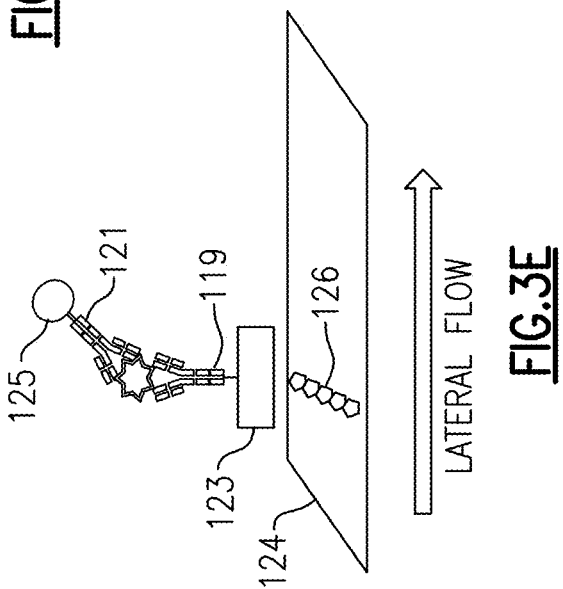
FIG.3D
FIG.3E
FIG.3C

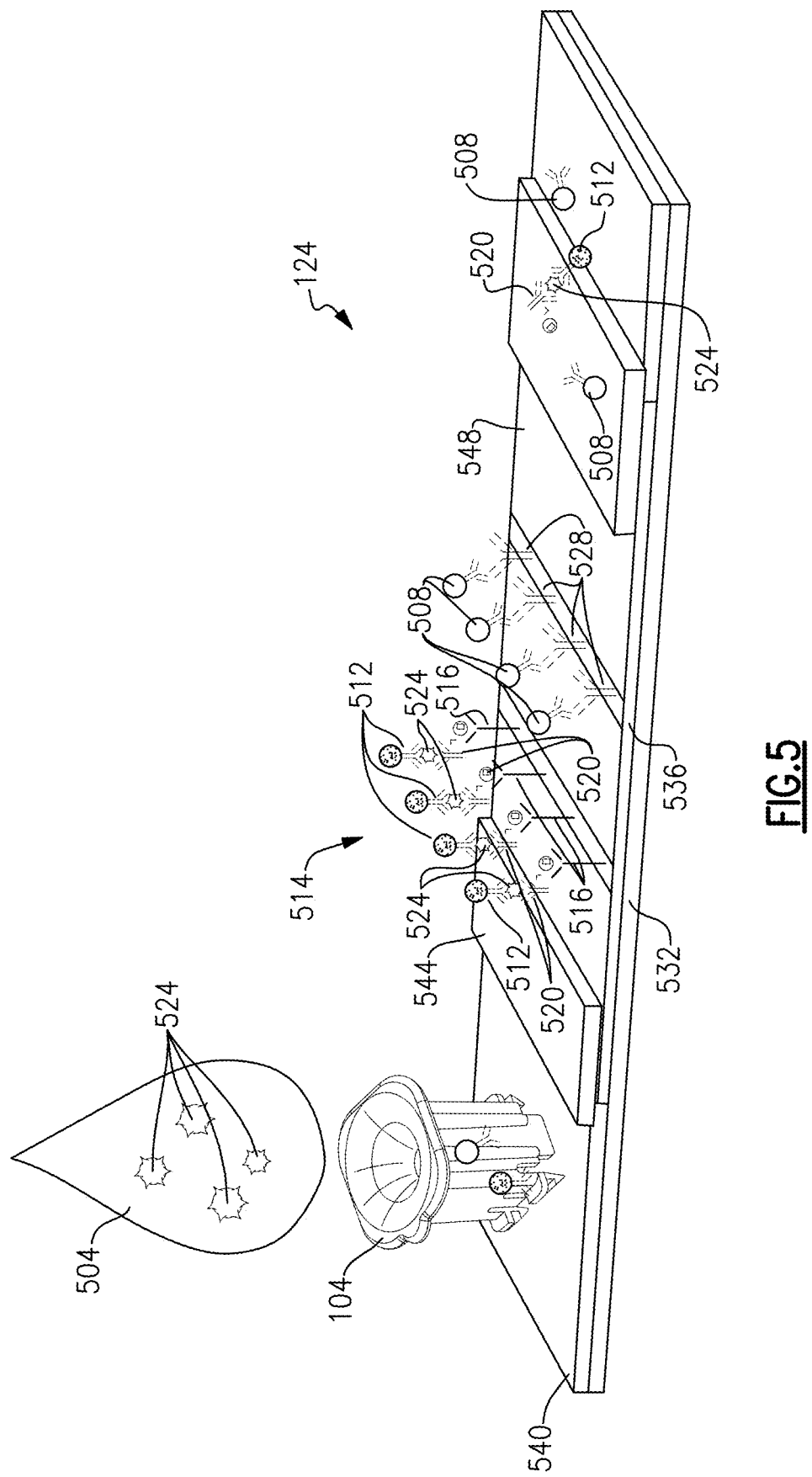

ated Applications

The present application claims priority to U.S. provisional application No. 63/373,531, filed Aug. 25, 2022, which is incorporated by reference herein in its entirety.

FIELD

The disclosed technology generally relates to diagnostic assay devices, kits including the same and methods of using the same, and more particularly to diagnostic assay devices having a microreactor, diagnostic assay kits including the same and methods of using the same.

DESCRIPTION OF THE RELATED ART

Diagnostic assays such as immunoassays include bioanalytical methods in which an analyte is detected based on a reaction with a capture molecule. For example, in some immunoassays, the detection of an antigen may be based on the reaction thereof with an antibody. Diagnostic assays have been widely used in many important areas such as diagnosis of diseases, therapeutic drug monitoring, clinical pharmacokinetic and bioequivalence studies in drug discovery and pharmaceutical industries, to name a few. The importance and widespread use of diagnostic assays in pharmaceutical analysis are attributed to their specificity, high-throughput, and high sensitivity for the detection of a wide range of analytes in biological samples.

SUMMARY

In one aspect, a diagnostic assay device for detecting an analyte in a sample solution comprises a microreactor configured to flow therethrough in a first direction the sample solution containing the analyte and react the analyte with a capture molecule to form an analyte-capture molecule complex, and to transfer the sample solution to an absorbent strip pad. The absorbent strip pad is configured to flow therethrough, in a second direction crossing the first direction, the sample solution including the analyte-capture molecule complex formed in the microreactor and indicate a presence of the analyte-capture molecule complex.

In another aspect, a diagnostic assay device for detecting an analyte in a sample solution comprises a microreactor configured to flow in a first direction the sample solution containing the analyte through a porous wicking filter to form therein an analyte-capture molecule complex, and to transfer the sample solution to an absorbent strip pad. The absorbent strip pad is configured to flow therethrough, in a second direction crossing the first direction, the sample solution including the analyte-capture molecule complex formed in the microreactor and indicate a presence of the analyte-capture molecule complex.

In another aspect, a diagnostic assay device for detecting an analyte in a sample solution comprises a microreactor configured to receive a sample specimen containing the analyte and cause the sample specimen to contact a porous wicking filter comprising a capture molecule to form therein a sample solution comprising an analyte-capture molecule complex, and to transfer the sample solution in a first direction to an absorbent strip pad. The absorbent strip pad is configured to flow therethrough, in a second direction crossing the first direction, the sample solution including the analyte-capture molecule complex formed in the microreactor and indicate a presence of the analyte-capture molecule complex.

In another aspect, a diagnostic assay device for detecting an analyte in a sample solution comprises a microreactor configured to form an analyte-capture molecule complex from a sample solution containing an analyte. The microreactor comprises a specimen-receiving region configured to receive a sample specimen comprising the analyte through a top opening for forming the sample solution therein. The specimen-receiving region is additionally configured to transfer the sample solution in a first direction through a bottom opening. The microreactor additionally comprises a reaction region disposed below the specimen-receiving region and configured to receive the sample solution through the bottom opening of the specimen-receiving region. The reaction region is additionally configured to form therein an analyte-capture molecule complex comprising the analyte specifically bound with a capture molecule. The reaction region is further configured to vertically transfer the sample solution including the analyte-capture molecule complex to an absorbent strip pad disposed underneath the reaction region.

In another aspect, a method of detecting an analyte in a sample solution comprises providing a diagnostic assay device comprising a microreactor. The method additionally comprises forming a sample solution containing the analyte and a buffer solution in the microreactor. The method additionally comprises causing the sample solution containing the analyte to flow in a first direction through the microreactor to form an analyte-capture molecule complex. The method further comprises causing the sample solution containing the analyte-capture molecule complex to be transferred to an absorbent strip pad configured to flow the sample solution therethrough, in a second direction crossing the first direction, the sample solution including the analyte-capture molecule complex formed in the microreactor, and to indicate a presence of the analyte-capture molecule complex.

In another aspect, a diagnostic assay kit for detecting an analyte in a sample solution comprises a specimen collection unit configured for collecting a sample specimen containing the analyte. The diagnostic assay kit additionally comprises a diagnostic assay device comprising a microreactor formed above an absorbent strip pad. The microreactor is configured to receive the sample specimen from the specimen collection unit, form therein a sample solution containing the analyte and flow the sample solution therethrough in a first direction to form an analyte-capture molecule complex. The microreactor is further configured to transfer the sample solution to an absorbent strip pad configured to flow therethrough, in a second direction crossing the first direction, the sample solution including the analyte-capture molecule complex formed in the microreactor and indicate a presence of the analyte-capture molecule complex. The assay kit further comprises a buffer solution configured to be mixed with the sample specimen to form the sample solution in the microreactor.

In some embodiments, diagnostic assay devices for detecting an analyte in a sample specimen are provided. The devices may comprise a microreactor and an absorbent strip pad. In some embodiments the microreactor comprises a specimen-receiving chamber vertically above and fluidly connected to a reaction chamber, the reaction chamber having a cylindrical volume housing a porous wicking filter, the porous wicking filter comprising a plurality of capture molecules adapted to specifically bind to the analyte in the sample solution and form an analyte-capture molecule complex. In some embodiments the porous wicking filter comprises capture molecules at a concentration of 0.1 to 2 mg/ml in the sample solution. The analyte is an antigen and the capture molecule comprises an antibody or portion thereof in some embodiments. For example, the analyte may be a SARS-CoV-2, RSV, influenza A or influenza B antigen and the capture molecule may be a SARS-CoV-2, RSV, influenza A or influenza B antibody, respectively.

The microreactor may be configured to receive a sample specimen containing the analyte and a buffer solution in the specimen-receiving chamber to form a sample solution and flow the sample solution in a first direction to contact the porous wicking filter in the reaction chamber and form therein the analyte-capture molecule complex, and to transfer the sample solution containing the analyte-capture molecule complex to the absorbent strip pad. In some embodiments, the porous wicking filter is configured to contact the sample solution at an upper end thereof and contact the absorbent strip pad at a lower end thereof.

The absorbent strip is in contact with the porous wicking filter and may be configured to configured to flow therethrough, in a second direction crossing the first direction, the sample solution including the analyte-capture molecule complex and indicate a presence of the analyte-capture molecule complex. In some embodiments the absorbent strip pad is configured to transfer the sample solution in the second direction substantially by capillary action. In some embodiments the first direction is a vertical direction, or within about 45° of vertical with respect to the direction of the direction of the force of gravity and the second direction may be a horizontal direction, or within about 45° of horizontal, with respect to the direction perpendicular to the direction of the force of gravity. The absorbent strip pad may be substantially free of capture molecules and/or detection molecules prior to flowing the sample solution therethrough.

In some embodiments the specimen-receiving chamber comprises an upper portion having a wide top opening adapted to receive a sample specimen comprising the analyte, and a lower portion comprising a cylindrical cavity and a bottom opening adjacent to the reaction chamber, wherein the upper portion is wider than the lower portion and the bottom opening has a diameter narrower than the diameter of the cylindrical cavity. The specimen receiving chamber may have a funnel shape, where the lower portion is configured to hold a limited volume of the sample solution and the upper portion configured to hold an excess volume of the sample solution in excess of the limited volume. Thus, in some embodiments the lower portion of the specimen-receiving chamber may have a smaller volume than the total volume of the sample solution. In some embodiments, the lower portion of the specimen-receiving chamber may have a volume of about 100-300 µl, such as when a total volume of the sample solution is about 100-350 µl.

In some embodiments the specimen-receiving chamber is configured to receive and extract the sample specimen from a swab comprising the sample specimen. The lower portion of the specimen-receiving chamber may be configured to stop and hold the swab when it is inserted.

In some embodiments, the reaction chamber is configured to receive the sample solution from the specimen-receiving region and facilitate the transfer of the sample solution to the absorbent strip pad in part using gravity. The porous wicking filter may additionally comprise a plurality of detection molecules comprising a colorimetric component and adapted to specifically bind to the analyte and/or the analyte-capture molecule complex. In some embodiments, the porous wicking filter comprises detection molecules at a concentration of about 0.001 to 0.1% in the sample solution. The colorimetric component may be any of a variety of materials, such as a dye, of a cellulose nano bead, colloidal gold, a gold nano shell or a latex bead. In some embodiments, the porous wicking filter comprises detection molecules at a concentration of about 0.001 to 0.1% in the sample solution. The absorbent strip pad can receive the sample solution comprising an analyte-capture complex and detection molecule from the reaction chamber and transfer the sample solution in a lateral direction to cause a visual indication of a presence of the analyte-capture molecule complex. In some embodiments, the absorbent strip pad comprises a test line, where the test line comprising a plurality of binding molecules adapted to bind the analyte-capture molecule complex, such that the presence of analyte-capture molecule complexes can be visualized at the test line.

In some embodiments, the porous wicking filter comprises an elongated portion in which an upper portion proximal to the specimen-receiving chamber has a higher concentration of one or both of the capture molecules or detection molecules relative a lower portion proximal to the absorbent strip pad. The entire concentrations of one or both of capture molecules and/or detection molecules may be confined within an upper 50% of a length of the porous wicking filter. In some embodiments, the porous wicking filter comprises an elongated portion in which an upper portion proximal to the specimen-receiving chamber has one or both of the capture molecules or detection molecules while a lower portion proximal to the absorbent strip pad is free of one or both of the capture molecules or dye molecules.

In some embodiments, the porous wicking filter has a microstructure including porosity such that the reaction region is configured to facilitate the transfer of the sample solution from the specimen-receiving region to the absorbent strip pad in part by capillary action in addition to gravity. The porous wicking filter may be formed of a polymeric material. In some embodiments the porous wicking filter comprises an irregular structure of fibers and may have a packing density of about 0.35 g/cc.

In some embodiments diagnostic assay devices for detecting an analyte in a sample comprise a specimen-receiving chamber vertically above and fluidly connected to a reaction chamber, where the reaction chamber comprises a porous wicking filter. The porous wicking filter may be impregnated with a plurality of capture molecules adapted to specifically bind to the analyte and form an analyte-capture molecule complex and a plurality of detection molecules comprising a colorimetric component and adapted to specifically bind to the analyte-capture molecule complex. The devices may also comprise an absorbent strip pad that is in contact with the porous wicking filter. The specimen receiving chamber may comprise an upper portion having a wide top opening and a lower portion comprising a cylindrical cavity. In some embodiments the upper portion is wider than the lower portion. In some embodiments the porous wicking filter is oriented along a first axis and the absorbent strip pad is oriented along a second axis crossing the first axis. For example, the porous wicking filter may be oriented along a vertical axis, or within about 45 degrees of a vertical axis, and the absorbent strip pad may be oriented along a horizontal axis, or within about 45 degrees of a horizontal axis.

In some embodiments a diagnostic assay kit is provided, comprising a specimen collection unit for collecting a sample specimen containing an analyte; a diagnostic device as described herein, comprising a microreactor and an absorbent strip pad; and a buffer solution. In some embodiments the microreactor comprises a specimen-receiving chamber vertically above and fluidly connected to a reaction chamber, the reaction chamber having a cylindrical volume housing a porous wicking filter, the porous wicking filter comprising a plurality of capture molecules adapted to specifically bind to the analyte in the sample solution and form an analyte-capture molecule complex. The microreactor may be configured to receive a sample specimen containing the analyte and a buffer solution in the specimen-receiving chamber to form a sample solution and flow the sample solution in a first direction to contact the porous wicking filter in the reaction chamber and form therein the analyte-capture molecule complex, and to transfer the sample solution containing the analyte-capture molecule complex to the absorbent strip pad. The absorbent strip pad may be configured to flow therethrough, in a second direction crossing the first direction, the sample solution including the analyte-capture molecule complex and indicate a presence of the analyte-capture molecule complex. In some embodiments the specimen collection unit comprises a swab configured to be wetted with the sample specimen.

In some embodiments methods for identifying the presence of an analyte in a sample specimen are provided. A device is provided comprising a microreactor and an absorbent strip pad. The microreactor may comprise a specimen-receiving chamber vertically above and fluidly connected to a reaction chamber, the reaction chamber having a cylindrical volume and housing a porous wicking filter. The porous wicking filter comprises a plurality of capture molecules adapted to specifically bind to the analyte. In some embodiments the porous wicking filter comprises capture molecules at a concentration of 0.1 to 2 mg/ml in the sample solution.

The absorbent strip pad is in contact with the porous wicking filter. In the methods a sample specimen and a buffer solution are placed in the specimen-receiving chamber and form a sample solution. The sample solution is flowed through the microreactor in a first direction to contact the porous wicking filter in the reaction chamber. The analyte capture molecules react with analyte in the sample solution to form an analyte-capture molecule complex in the sample solution. The sample solution is then transferred to the absorbent strip pad, where it flows through the absorbent strip pad in a second direction crossing the first direction. In some embodiments the absorbent strip pad transfers the sample solution in the second direction substantially by capillary action. The analyte-capture molecule complex is detected in the absorbent strip pad to identify the presence of the analyte in the sample specimen. The first direction may be a vertical direction substantially parallel to the direction of the force of gravity, or within about 45° of vertical with respect to the direction of the direction of the force of gravity and the second direction may be a horizontal direction substantially perpendicular to the direction of the force of gravity, or within about 45° of horizontal, with respect to the direction perpendicular to the direction of the force of gravity.

In some embodiments the absorbent strip pad is substantially free of capture molecules and/or detection molecules prior to forming the sample solution.

In some embodiments the sample is obtained from a patient, such as a human patient, and may comprise, for example, one or more of blood, urine, serum, plasma, saliva, cerebral spinal fluid, nasal secretions, pharyngeal secretions, urethral secretions and vaginal secretions. The sample may be obtained with a swab, such as by wetting a swab with the sample specimen. The swab may be inserted into the sample-receiving chamber, and in some embodiments mechanical energy is applied to the swab to cause the analyte to be extracted from the swab and mixed with the buffer solution.

In some embodiments the specimen-receiving chamber comprises an upper portion having a wide top opening adapted to receive a sample specimen comprising the analyte, and a lower portion comprising a cylindrical cavity and a bottom opening adjacent to the reaction chamber, wherein the upper portion is wider than the lower portion and the bottom opening has a diameter narrower than the diameter of the cylindrical cavity. The lower portion of the specimen-receiving chamber may stop and hold the swab inserted into the specimen-receiving region.

In some embodiments, the specimen-receiving chamber has a funnel shape, and the lower portion is configured to hold a limited volume of the sample solution and the upper portion is configured to hold an excess volume of the sample solution in excess of the limited volume. For example, the lower portion of the specimen-receiving chamber may have a volume of about 100-300 μl when a total volume of the sample solution is about 100-350 μl. Excess sample solution may be retained in the funnel shaped upper portion 108A-2 of the specimen-receiving chamber until it is able to move through the lower portion 108A-1 and the porous wicking filter 116 as the sample solution flows through the device.

In some embodiments the porous wicking filter contacts the sample solution at an upper end thereof and contacts the absorbent strip pad at a lower end thereof. The sample solution is transferred to the absorbent strip from the porous wicking filter at least in part using gravity. However, in some embodiments the sample may be transferred to the absorbent strip using capillary action in addition to gravity.

In some embodiments the porous wicking filter comprises detection molecules comprising a colorimetric component and adapted to specifically bind to the analyte and/or the analyte-capture molecule complex. The detection molecules may be present at a concentration of about 0.001 to 0.1% in the sample solution in some embodiments. The colorimetric component may be, for example a dye, a cellulose nano bead, a gold nano shell or a latex bead.

In some embodiments the absorbent strip pad receives the sample solution from the reaction chamber and transfers the sample solution in a lateral direction to cause a visual indication of a presence of the analyte-capture molecule complex. The absorbent strip pad may comprise a test line impregnated with a plurality of binding molecules adapted to bind the analyte-capture molecule complex. Thus, the analyte-capture molecule complex in the absorbent strip pad may be detected by visualizing bound analyte-capture molecule complexes at the test line.

In some embodiments the analyte is an antigen, and the capture molecule comprises an antibody or portion thereof. In some embodiments the analyte is a SARS-CoV2 antigen, the capture molecule is a SARS-CoV2 antibody, and the method is used to identify the presence of SARS-CoV2 in a patient sample. In some embodiments the analyte is an RSV antigen, the capture molecule is an RSV antibody, and the method is used to identify the presence of RSV in a patient sample. In some embodiments the analyte is an influenza A antigen, the capture molecule is an influenza A antibody, and the method is used to identify the presence of influenza A in a patient sample. In some embodiments the analyte is an influenza B antigen, the capture molecule is an influenza B antibody, and the method is used to identify the presence of influenza B in a patient sample.

In some embodiments methods for identifying the presence of an analyte in a sample comprise providing device comprising a microreactor and an absorbent strip pad. The microreactor may comprise a specimen-receiving chamber vertically above and fluidly connected to a reaction chamber, the reaction chamber housing a porous wicking filter impregnated with a plurality of capture molecules adapted to specifically bind to the analyte and form an analyte-capture molecule complex and a plurality of detection molecules comprising a colorimetric component and adapted to specifically bind to the analyte-capture molecule complex. The absorbent strip pad is in contact with the porous wicking filter. Further the absorbent strip pad may comprise a plurality of binding molecules on a test line, where the binding molecules are adapted to bind the analyte-capture molecule complex.

A sample specimen and buffer solution are placed in the sample-receiving chamber to form a sample solution and the sample solution flows through the microreactor in a first direction to contact the porous wicking filter and form analyte-capture molecule complexes therein. The sample solution containing the analyte-capture molecule complexes is transferred to the absorbent strip pad and flow in a second direction crossing the first direction such that analyte-detection complexes are bound at the test line and can be visualized to identify the presence of the analyte in the sample specimen.

In some embodiments the first direction that the sample solution flows is a vertical direction within an angle of about 45° with respect to the direction of the direction of the force of gravity and the second direction that the sample solution flows is a horizontal direction within an angle of about 45° with respect to the direction perpendicular to the direction of the force of gravity.

In some embodiments the sample solution sample solution has a volume of 100-350 µl. The porous wicking filter may have a smaller volume, such as about 100 µl. In some embodiments the specimen-receiving chamber comprises an upper portion having a wide top opening adapted to receive the sample specimen comprising the analyte, and a lower portion comprising a cylindrical cavity having a volume of about 100-300 µl.

BRIEF DESCRIPTION OF THE DRAWINGS

FIG. 1A illustrates a cross sectional view of a diagnostic assay device having a microreactor configured for detecting an analyte in a sample solution, according to embodiments.

FIG. 1E illustrates perspective and cross-sectional views of the microreactor for the diagnostic assay device illustrated in FIGS. 1A and 1B, according to embodiments.

FIGS. 3A-3E schematically illustrate a diagnostic assay device at various stages of performing a method of detecting an analyte in a sample solution, according to embodiments.

FIG. 5 schematically illustrates, in operation, a diagnostic assay device having a microreactor configured for indication of a presence of the analyte-capture molecule complex, according to embodiments.

DETAILED DESCRIPTION

Figure 1B:
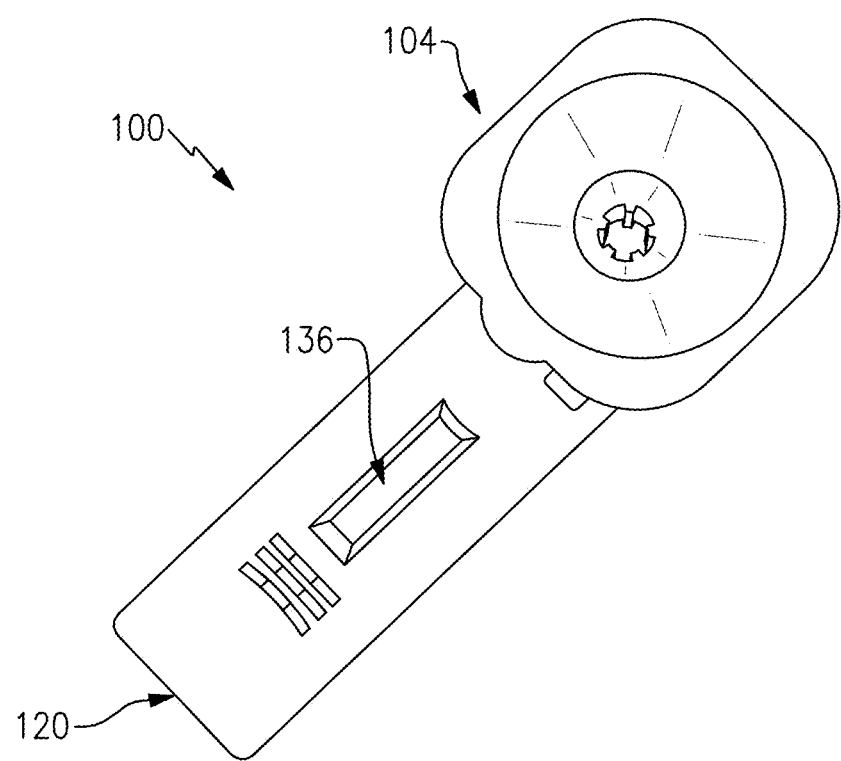
FIG. 1B illustrates a perspective photograph of the diagnostic assay device illustrated in FIG. 1A.

Diagnostic assays have been widely used in many important areas such as diagnosis of diseases, therapeutic drug monitoring, clinical pharmacokinetic and bioequivalence studies in drug discovery and pharmaceutical industries, to name a few. As disclosed herein, various devices and methods of using diagnostic assay devices may be described in reference to a specific application, e.g., a COVID-19 antigen test. However. it will be understood that the specific application is described by way of example only, and that devices and methods according to embodiments are not so limited to such specific application unless explicitly stated otherwise.

Quantitative reverse transcription polymerase chain reaction (RT-qPCR) is one of primary diagnostic methods for diagnoses of some viral infections, e.g., COVID-19 diagnosis. Advantages of RT-qPCR testing includes a relatively high analytical sensitivity. However, large-scale clinical laboratory testing requires a dedicated infrastructure and specialized technician training. In addition, due to the specimen transport and processing time, results for standard RT-qPCR can take a relatively long time to obtain.

In view of these shortcomings of RT-qPCR testing, to complement or supplement the RT-qPCR testing, antigen testing has been utilized either in conjunction with RT-qPCR as a first-line screening test or in decentralized health care settings in which RT-qPCR testing may not be conducive for rapid result turnaround. Antigen-based testing involves the application of specific antibodies in several assay formats, including lateral flow immunofluorescent sandwich assays, chromatogenic digital immunoassays, lateral flow immunoassays with visual read, and microfluidic immunofluorescence assays.

Rapid antigen-based lateral flow testing has been implemented globally to achieve rapid accurate and cost-effective results for diagnoses of infectious diseases including COVID-19. Many antigen tests are based on lateral flow assays, which are relatively inexpensive assays that use paper-based or plastic-based platforms to detect chemical or biological analytes within relatively short durations of time. By way of example, to begin a COVID-19 antigen test, e.g., a nasal swab is collected from the patient and soaked into a specimen-receiving solution that causes the virus to release its antigen proteins such as a nucleocapsid protein, a phosphoprotein, and/or a spike protein. A liquid sample of this specimen-receiving solution is then applied to a lateral flow test strip, where it migrates laterally therethrough and interact with antigen-specific antibodies that have been conjugated with visible indicators. If severe acute respiratory syndrome coronavirus-2 (SARS-CoV-2) antigens are present in the sample above a minimum detection level, they can be captured by the antigen-specific antibodies and visually observed as colored lines on the strip test, indicating a positive test for COVID-19. Despite the rapid and cost-effective results provided by rapid antigen-based lateral flow assays, challenges remain, including relatively high variance among different tests, relatively low sensitivity (high false negativity) and specificity (high false positivity), particularly at low viral loads, relatively low repeatability (and high false positivity) and susceptibility to misinterpretation of test results, e.g., compared to RT-qPCR assays.

The inventors have discovered that many of the shortcomings of existing lateral flow testing can be mitigated or overcome by improving the spatiotemporal extraction and concentration of the analyte to increase the amount of analyte-capture molecule complex formed from a given amount of sample specimen. The inventors have discovered that this objective can be achieved in part by increasing the efficiency of reaction between the analyte and the capture molecules, which can in turn be increased by simultaneously increasing the concentrations of the analyte and capture molecules. The inventors have surprisingly discovered that increasing the concentrations for a given amount of analyte and capture molecules is much more effective than increasing the amounts of the analyte and capture molecules. By increasing the concentrations, the relative amounts of the analyte and capture molecules that are mutually available for forming the analyte-capture molecule are commensurately increased, while reducing the relative amounts of unused analyte and capture molecules. Further, the inventors have discovered that it is advantageous to have volumes of highly concentrated analyte and highly concentrated capture molecules be disposed in close proximity to one another. The close proximity was found to not only advantageously reduce the time it takes for the sample specimen containing the analyte to pass through the capture molecules, but also to simultaneously increase the spatial overlap of high concentration regions of concentration profiles of the analyte and the capture molecules. These effects of close proximity were found to directly increase the sensitivity. In summary, by simultaneously increasing the concentrations of the capture molecules and analyte spatiotemporally, the efficiency of analyte-capture molecule complex formation can be significantly enhanced. The devices disclosed herein are adapted for these and other improvements and show sufficient sensitivity while using relatively small amounts of the sample specimen and/or analyte and capture molecule, by enabling relatively high proportions of the analyte and capture molecules to participate in complex formation compared to the existing devices.

To address these and other needs, a diagnostic assay device for detecting an analyte in a sample solution according to various embodiments comprises a microreactor connected to an absorbent strip pad. The microreactor is configured to receive a sample specimen containing the analyte and cause the sample specimen to contact a porous wicking filter comprising a capture molecule. The microreactor is configured to flow therethrough in a first direction, e.g., a vertical direction, the sample solution containing the analyte and react the analyte with the capture molecule to form an analyte-capture molecule complex, and to transfer the sample solution to an absorbent strip pad where the sample flows in a second direction crossing the first direction. For example, in some embodiments the porous wicking filter is oriented along a first axis and the absorbent strip pad is oriented along a second axis crossing the first axis. For example, the porous wicking filter may be oriented along a vertical axis, or within about 45 degrees of a vertical axis, and the absorbent strip pad may be oriented along a horizontal axis, or within about 45 degrees of a horizontal axis.

Advantageously, the microreactor is configured to form and flow highly concentrated sample solution through the microreactor having a high concentration of the capture molecule, thereby efficiently forming the analyte-capture molecule complex. In some embodiments capture molecules are only present in the microreactor, and are not present in the absorbent strip pad, prior to providing the sample solution containing the analyte. In some embodiments the wicking filter also comprises a detection molecule that is also specific for the analyte of interest, such as a detection antibody, and includes a colorimetric component, such as a tag or dye, to facilitate visualization of the analyte. The detection molecule may thus also react with the analyte and form part of the analyte-capture molecule complex.

The absorbent strip is configured to flow therethrough, in a second direction crossing the first direction, e.g., a horizontal direction, the sample solution including the analyte-capture molecule complex formed in the microreactor and indicate a presence of the analyte-capture molecule complex. In some embodiments the absorbent strip comprises a binding molecule at a test site or test strip, such that the analyte-capture molecule complex is immobilized at that location and can be visualized. Unlike existing lateral flow devices in which an analyte in a sample solution travels a significant distance in an absorbent strip pad, which may spatially dilute the analyte, before forming an analyte-capture molecule complex by reacting with a capture molecule disposed in the absorbent strip pad, the vertical flow microreactor according to embodiments is configured to form the analyte-capture molecule complex prior to coming into contact with an absorbent strip pad. In some embodiments the analyte also reacts with a detection molecule that becomes part of the analyte-capture molecule complex prior to coming into contact with the adsorbent strip pad.

Further, the analyte-capture molecule complex may be formed while the sample solution is flowing in a vertical direction, with the aid of gravity. The inventors have found that the vertical flow microreactor according to embodiments provides various advantageous control capabilities as described herein, including a spatial and temporal control of the movement and reaction of the analyte as it is transferred through the vertical flow microreactor to enhance the sensitivity, efficiency and speed of the analyte detection.

As described herein, an analyte refers to a molecule to be detected by a diagnostic assay such as an immunoassay. An analyte may be a protein or other kinds of molecules, of different sizes and types, that can form a complex with a capture molecule adapted to specifically bind to the analyte. In various diagnostic assays, it is the presence of an analyte-capture molecule complex that is actually detected, from which the presence of the analyte can be inferred. It will be appreciated that a molecule that is an analyte to be detected in one diagnostic assay can serve as a molecule that serves as a capture molecule in another diagnostic assay. For example, in the context of forming an antigen-antibody complex in an immunoassay, in some techniques, the analyte may be an antigen while the capture molecule may comprise an antibody or portion thereof. However, in some other techniques, the analyte may be an antibody while the capture molecule may be an antigen. Thus, as disclosed, unless stated otherwise, a molecule that can be an analyte in one technique can also serve as a capture molecule in another technique. Without limitation, according to various embodiments, an analyte or a capture molecule may be any one or more of amino acids, peptides, polypeptides, proteins, glycoproteins, lipoproteins, nucleosides, nucleotides, oligonucleotides, nucleic acids, sugars, carbohydrates, oligosaccharides, polysaccharides, fatty acids, lipid, hormones, metabolites, cytokines, chemokines, receptors, neurotransmitters, antigens, allergens, antibodies, substrates, cofactors, inhibitors, drugs, pharmaceuticals, nutrients, prions, toxins, poisons, explosives, pesticides, chemical warfare agents, biohazardous agents, bacteria, viruses, radioisotopes, vitamins, heterocyclic aromatic compounds, carcinogens, mutagens, narcotics, amphetamines, barbiturates, hallucinogens, waste products, contaminants, and mixtures thereof.

As described herein, an analyte detection molecule is a molecule that can bind to the analyte and/or the analyte-capture molecule complex and that facilitates visualization of the analyte-capture molecule complex. In some embodiments the analyte detection molecule may comprise a detection component, such as a colorimetric component, for example a fluorophore or colorimetric dye or structure. The colorimetric component may be, for example, a compound, particle, structure or other tag that allows for visualization of the analyte-capture molecule complex. The detection molecule may comprise, for example, an antibody or portion thereof that binds to the analyte and/or the analyte-capture molecule complex and that is detectably labelled. In some embodiments one or more antibodies (or portions thereof) that specifically bind the analyte or the analyte-capture molecule complex may be conjugated to a particle that can be visualized, such as a colorimetric or fluorescent particle. In some embodiments the detection molecule may comprise cellulose nanobeads. In some embodiments the detection molecule may comprise colloidal gold. In some embodiments the detectable molecule may comprises a gold nano shell. In some embodiments the detection molecule may comprise a colored latex bead.

As described herein, a sample specimen refers to a biological material to be analyzed for the presence of an analyte of interest. In some embodiments the sample specimen is from a human. In some embodiments the sample specimen may be from an animal. In some embodiments the sample specimen may be from a plant. In some embodiments the sample specimen is obtained from a patient. In some embodiments the patient may be a human patient. In some embodiments the patient may be an animal patient. Sample specimens may include but are not limited to blood, urine, serum, plasma, saliva, cerebral spinal fluid, nasal secretions, pharyngeal secretions, urethral secretions and vaginal secretions to name a few.

As described herein, a sample solution refers to any intermediate solution formed from a sample specimen at various stages of a diagnostic assay. For example, a mixture of a sample specimen and a buffer solution, as well as a solution comprising an analyte-capture molecule complex may be referred to herein as a sample solution.

As described herein, the term vertical, e.g., as it may be used in the context of a flow direction of a liquid such as a sample solution, will be understood to mean directions that are substantially parallel, e.g., within ±45°, to the vector direction of the force of gravity of the earth, or directions that are substantially perpendicular to the ground plane. For example, a sample solution flowing in a vertical direction may flow in a direction that is within an angle, with respect to the gravity vector direction, of ±45°, ±30°, ±15°, ±10°, ±5°, or an angle within a range defined by any of these values.

Similarly, as described herein, the term horizontal or lateral, e.g., as it may be used in the context of a flow direction of a liquid such as a sample solution, will be understood to mean directions that are substantially parallel, e.g., within ±45°, to a direction perpendicular to the vector direction of the force of gravity of the earth, or directions that are substantially parallel to the ground plane. For example, a sample solution flowing in a horizontal or lateral direction may flow in a direction that is within an angle, with respect to the direction perpendicular to the gravity vector direction, of ±45°, ±30°, ±15°, ±10°, ±5°, or an angle within a range defined b any of these values.

FIG. 1A illustrates a cross sectional view of a diagnostic assay device having a microreactor configured for detecting an analyte in a sample solution, according to embodiments. The illustrated diagnostic assay device 100 for detecting an analyte in a sample solution comprises a microreactor 104 configured as a dual-chamber microreactor for flowing the sample solution therethrough in a first direction, e.g., a vertical direction. The microreactor 104 is configured to form an analyte-capture molecule complex from a sample solution containing an analyte. The microreactor 104 comprises a specimen-receiving chamber (or region) 108 configured to receive a sample specimen to be tested for the presence of the analyte, e.g., from a swab wetted with a sample specimen, through a top opening for forming the sample solution therein. The specimen-receiving chamber 108 is additionally configured to transfer the sample solution through a bottom opening in a second direction, e.g., a vertical direction. The microreactor 104 additionally comprises a reaction chamber (or region) 112 disposed vertically below and fluidly connected to the specimen-receiving chamber 108 and configured to receive the sample solution through the bottom opening of the specimen-receiving chamber 108. The reaction chamber 112 is additionally configured to form therein an analyte-capture molecule complex comprising the analyte specifically bound with a capture molecule, which can include, e.g., a capture antibody and/or a detection antibody. The reaction chamber 112 is further configured to transfer the sample solution including the analyte-capture molecule complex, e.g., in the vertical direction, to an absorbent strip pad 124 disposed underneath the reaction chamber 112.

In some embodiments the absorbent strip pad 124 comprises one or more molecules that allow for the visualization of the analyte-capture molecule complex at a test area or test line. For example, the absorbent strip may comprise a test line, the test line comprising one or more binding molecules that bind the analyte-capture molecule complex, for example by binding a portion of the capture molecule in the analyte-capture molecule complex, with specificity in order to immobilize the analyte-capture molecule complex on the test line. In some embodiments the capture molecule may comprise biotin and the binding molecule may comprise streptavidin. The absorbent strip pad 124 may also comprise a control area or control line for the binding of a control capture molecule, such as a control antibody.

The diagnostic assay device 100 comprises outer casings enclosing various components thereof. The specimen receiving chamber 108 and reaction chamber 112 are enclosed within a microreactor casing 116. The absorbent strip pad 124 is enclosed by an upper casing 128 and a lower casing 132. The upper casing 128 has formed therethrough a viewing window 136 for visual indication, e.g., a test line, indicative of a presence of an analyte-capture molecule complex.

FIG. 1B illustrates a perspective photograph of the diagnostic assay device 100 illustrated in FIG. 1A. The absorbent strip pad 124 is visible though the viewing window 136.

Figure 1D:
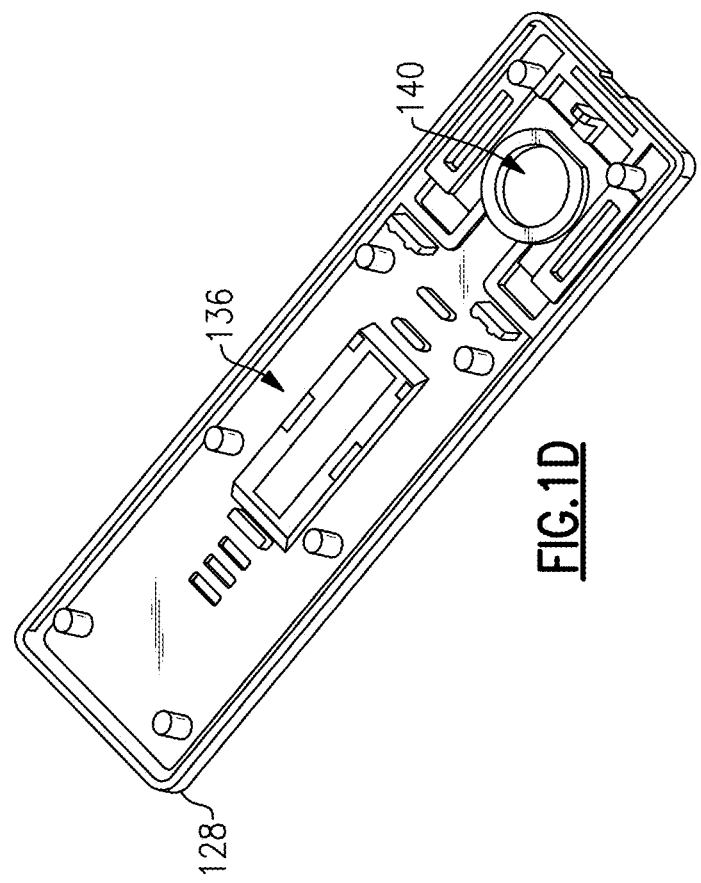
FIG. 1D illustrates a perspective inside view of an upper casing of the diagnostic assay device illustrated in FIGS. 1A and 1B.
Figure 1C:
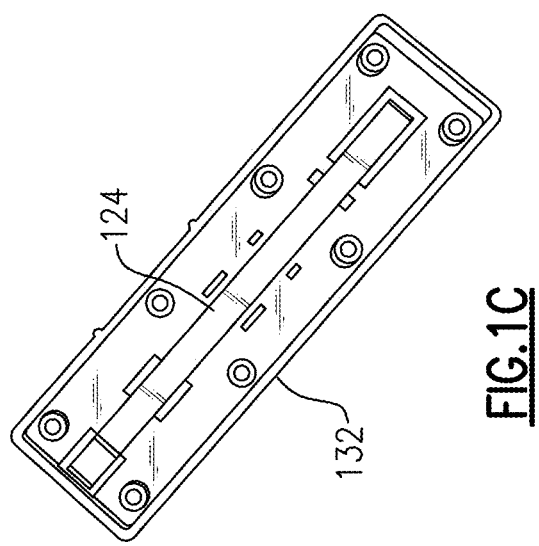
FIG. 1C illustrates a perspective photograph of a lower casing disposed therein an absorbent strip pad of the diagnostic assay device illustrated in FIGS. 1A and 1B.

FIG. 1C illustrates a perspective photograph of the lower casing 132 having disposed therein the absorbent strip pad 124 of the diagnostic assay device 100 illustrated in FIGS. 1A and 1B. As shown, the absorbent strip pad 124 is elongated for laterally transferring the sample solution by capillary action.

FIG. 1D illustrates a perspective inside view of the upper casing 128 of the diagnostic assay device 100 illustrated in FIGS. 1A and 1B. The upper casing 128 has the viewing window 136 at a midportion thereof configured to expose the visual inspection area of the absorbent strip pad 124. The upper casing 128 additionally has a receiving opening 140 for receiving the sample solution including the analyte-capture molecule complex from the microreactor 104, for transferring the sample solution to the absorbent strip pad 124, which in turn is configured to laterally flow therethrough the sample solution including the analyte-capture molecule complex and indicate a presence of the analyte-capture molecule complex.

Advantageously, the microreactor 104 is removably attached to the upper casing 128 using a suitable fixing or latching mechanism. Furthermore, the upper and lower casings 132 and 128 are detachably attached to each other. As such, parts of the microreactor 104 can be reused. For example, upon replacing consumable parts, e.g., the absorbent strip pad 124 and/or a porous wicking filter (FIG. 1E), the remaining parts can be reused.

Figure 4B:
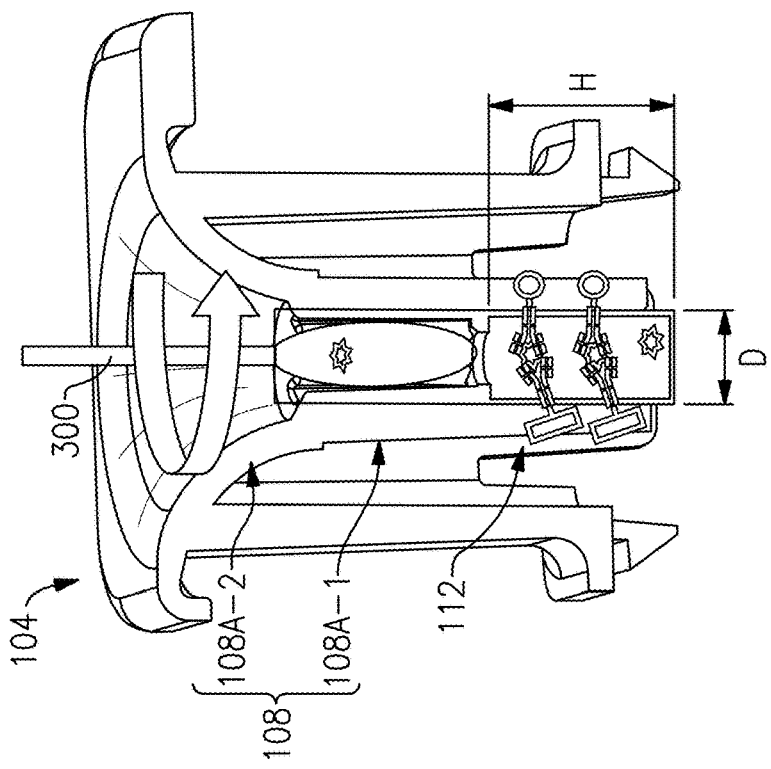
FIGS. 4A and 4B schematically illustrate advantageous arrangements of a vertical flow microreactor of a diagnostic assay device, according to embodiments.
Figure 4A:
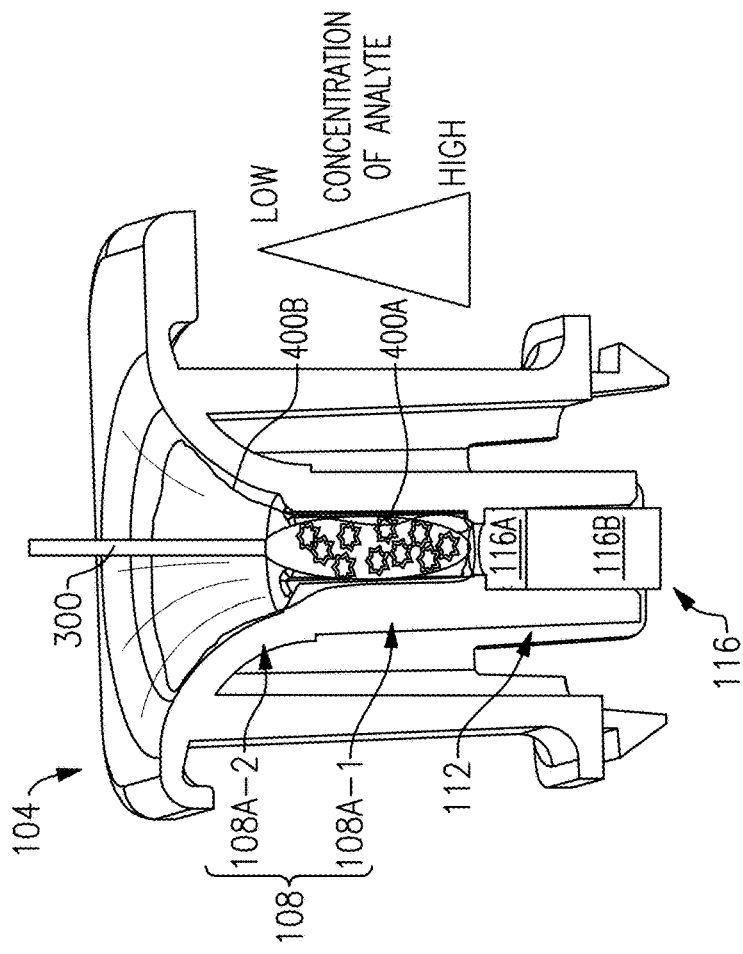

FIG. 1E illustrates perspective and cross-sectional views of the microreactor for the diagnostic assay device illustrated in FIGS. 1A and 1B, according to embodiments. Illustrated on the left are top and bottom perspective views of the microreactor 104 illustrated in FIGS. 1A and 1B. Illustrated on the right is a cross-sectional view of the microreactor 104. As described above, the internal cavity of the microreactor 104 is divided into the specimen-receiving chamber 108 and the reaction chamber 112. The illustrated specimen-receiving chamber 108 has a funnel shape and can in turn be divided into a lower portion 108A-1 and an upper portion 108A-2, as shown in FIG. 4A. The upper portion 108A-2 has a wide upper opening adapted to effectively receive a sample specimen, e.g., via a wetted swab, therethrough. The upper opening continues to narrow towards the lower portion 108A-1, which comprises a cylindrical cavity. The lower portion 108A-1 is configured to hold a limited volume of the sample solution and designed to concentrate the analyte therein, while the upper portion 108A-2 is wider than the lower portion 108A-1 and is configured to hold an excess volume of the sample solution in excess of the limited volume filling the lower portion 108A-1. In some embodiments, the length of the lower portion 108A-1 may substantially correspond to the length of the wettable tip portion of the swab. In some embodiments such as the illustrated arrangement, the sidewalls of the lower portion 108A-1 may have protrusions or ridges designed to enhance extraction of the sample specimen from a rotating swab inserted thereinto. The lower portion 108A-1 is adjacent, e.g., immediately above, and fluidly connected to the reaction chamber 112. Separating the lower portion 108A-1 and the reaction chamber 112 is a lip portion 110 of the reaction chamber 112. The lip portion 110 has a diameter that is narrower than that of the lower portion 108A-1 and is configured to stop the wetted swab inserted into the lower portion 108A-1 and/or stop a porous wicking filter 116 inserted into the reaction chamber 112 as described below.

Still referring to FIG. 1E, the reaction chamber 112 of the microreactor 104 is configured to receive the sample solution from the specimen-receiving chamber 108. Below the lip portion 110, the reaction chamber 112 comprises a cylindrical volume. The reaction chamber 112 has a bottom opening 118, through which the sample solution is transferred to the absorbent strip pad 120 (FIG. 1A) in part with the aid of gravity. The bottom opening 118 has a diameter that is less than the diameter of the cylindrical volume 112. The cylindrical volume of the reaction chamber 112 houses a porous wicking filter 116 therein, which comprises, e.g., is impregnated with, the capture molecule, e.g., capture antibody, such as a biotin-linked antibody, and/or detection molecule, such as a colorimetric dye-linked antibody, for example a blue-CNB dye-linked antibody, for complexing with the analyte. FIG. 1E illustrates an exemplary capture molecule 119, which comprises a binding component 123 that can be used to immobilize the analyte-capture molecule complex. FIG. 1E also illustrates a detection molecule 121, which can bind to the analyte and/or the analyte-capture molecule complex and comprises a detection component 125 that can be used to visualize the immobilized analyte-capture molecule complex.

The porous wicking filter 116 extends vertically through the cylindrical volume of the reaction chamber 112. The porous wicking filter 116 is stopped by the lip portion 110 and configured to contact the sample solution at an upper end thereof. The diameter of the lip portion 110 controls the area of the porous wicking filter 116 exposed to the sample solution and may be adjusted to control the flow rate thereof. The porous wicking filter 116 is flush with or protrudes out of the bottom opening 118 of the reaction chamber 112, such that the porous wicking filter 116 contacts the absorbent strip pad 120 (FIG. 1A) at a lower end thereof. In some embodiments the capture molecule is present only in the wicking filter and is not present in the absorbent strip pad prior to application of the sample. In some embodiments the detection molecule is present only in the wicking filter and is not present in the absorbent strip pad prior to application of the sample.

It will be appreciated that, while in the illustrated diagnostic assay device 100 the microreactor 104 has the lip portion 110 demarcating the specimen-receiving chamber 108 and the reaction chamber 112, embodiments are not so limited. In other configurations, the specimen-receiving chamber 108 and the reaction chamber 112 may not have such demarcation and may be integrated as a single volume. In these configurations, the specimen-receiving chamber or region 108 and the reaction chamber or region 112 may be demarcated by the porous wicking filter 116 partly occupying the single volume, such that the volume above the porous wicking filter 116 is configured to serve as the specimen-receiving chamber or region 108, and the volume occupied by the porous wicking filter 116 is configured to serve as the reaction chamber or region 112, as described herein.

It will be appreciated that, while in the illustrated diagnostic assay device 100, the microreactor 104 is configured to flow the sample solution through the specimen-receiving chamber 108 and the reaction chamber 112 in a vertical direction that is substantially perpendicular to the direction in which the sample solution laterally flows through the absorbent strip pad 120, embodiments are not so limited. As described above, in some other implementations, the flow direction of the sample solution through one of both of the specimen-receiving chamber 108 and the reaction chamber 112 can be sloped or slanted with respect to the vertical direction, e.g., within ±45° of the direction of the vector direction of the force of gravity of the earth, and similarly, the flow direction of the sample solution through one of both of the specimen-receiving chamber 108 and the reaction chamber 112 can be sloped or slanted with respect to the horizontal direction, e.g., within ±45° of the direction perpendicular to the vector direction of the force of gravity of the earth.

Figure 2:
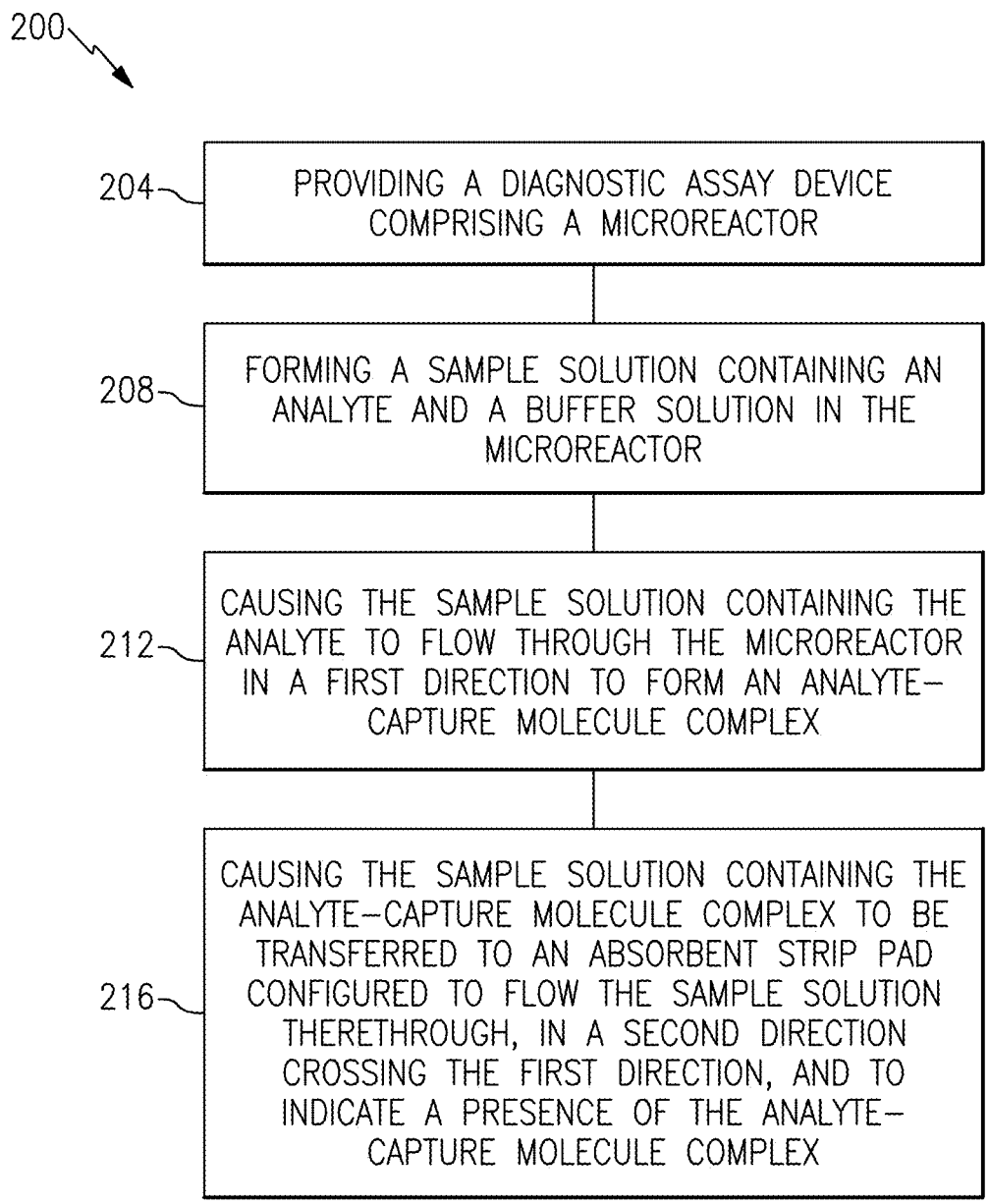
FIG. 2 illustrates a flowchart illustrating a method of detecting an analyte in a sample solution using a diagnostic assay device according to embodiments.

FIG. 2 provides a flowchart illustrating a method of detecting an analyte in a sample specimen using a diagnostic assay device according to embodiments. The flow chart is described alongside FIGS. 3A-3E, which schematically illustrate the diagnostic assay device at various stages of performing the method illustrated in the flowchart of FIG. 2.

The method 200 includes providing 204 a diagnostic assay device comprising a microreactor. The diagnostic device can be in accordance with any of the various embodiments disclosed herein, e.g., the diagnostic device 100 including a microreactor 104 as described above with respect to FIG. 1A. In some embodiments the diagnostic assay device comprises a microreactor comprising a specimen-receiving chamber vertically above and fluidly connected to a reaction chamber, the reaction chamber having a cylindrical volume and housing a porous wicking filter, the porous wicking filter comprising a plurality of capture molecules adapted to specifically bind to the analyte, and an absorbent strip pad that is in contact with the porous wicking filter.

Figure 3A:
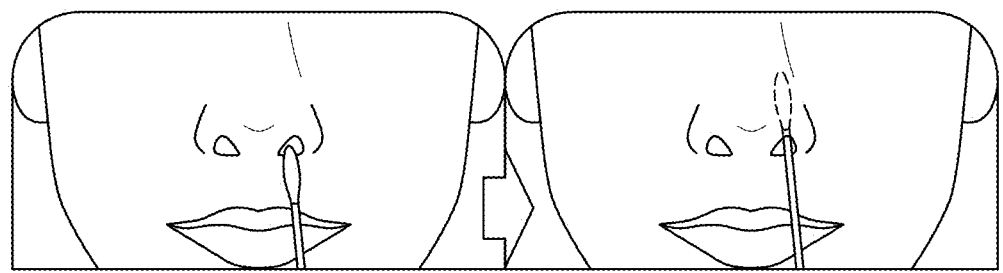
Figure 3B:
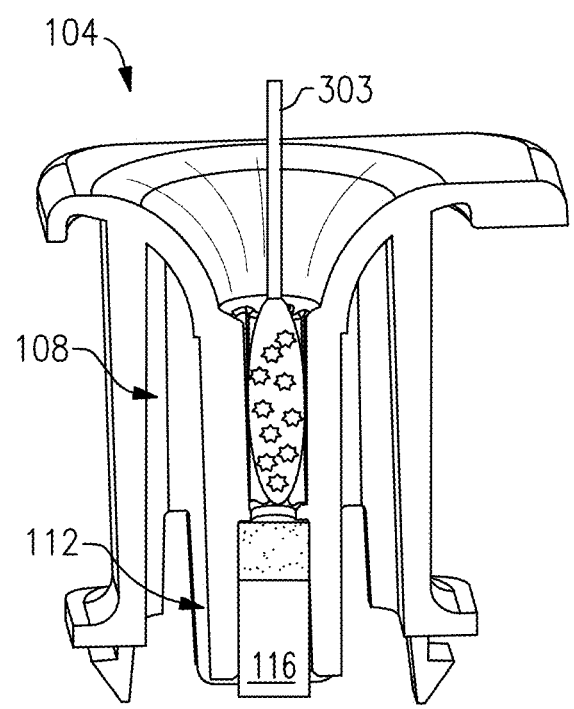

The method 200 additionally includes forming 208 a sample solution containing the analyte. The sample solution may be formed by placing a sample specimen and a buffer solution into the microreactor, for example in the specimen-receiving chamber of the microreactor. In some embodiments the sample solution is formed by wetting a swab with a sample specimen including the analyte and inserting the wetted swab and a buffer solution into the microreactor. In one implementation, wetting the swab with a sample specimen may include wetting the swab 300 with a nasal specimen, as illustrated in FIG. 3A. The swab 300 wetted with the sample specimen and comprising analyte 117 can then be inserted into the microreactor 104, as shown in FIG. 3B. As shown, it may be advantageous to have the length of the lower portion 108A-1 of the specimen-receiving chamber 108 substantially correspond to the length of the wettable tip portion of the swab 300 such that the sample solution formed therein is highly concentrated with the analyte.

Referring to FIG. 3C, after inserting the specimen, e.g., via a wetted swab 300, into the specimen-receiving chamber 108, a buffer solution 304 may be added to form a sample solution comprising a mixture of the buffer solution 304 and the sample specimen. In some implementations, the buffer solution 304 may be added in an amount, e.g., 5-20 drops or about 10 drops, which can be an entire premeasured volume provided in a separate vial, such that the resulting sample solution does not substantially exceed the volume of the lower portion 108A-1 of the specimen-receiving chamber 108 (with reference to FIG. 4A). In some embodiments the buffer solution is added such that a sample solution with a volume of about 100-350 µl is formed. The lower portion 108A-1 (FIG. 4A) may be designed to have a limited volume such that the sample solution can be highly concentrated with the analyte, while avoiding unnecessary dilution that may lower the sensitivity. The limited volume of the sample solution filling the lower portion 108A-1 of the specimen-receiving chamber 108 may be, e.g., 10-30 µl, 30-50 µl, 50-70 µl, 70-90 µl, 90-110 µl, 110-130 µl, 130-150 µl, 150-170 µl, 170-200 µl, 150-300 µl or a value in a range defined by any of these values. In some embodiments, the lower portion 108A-1 may hold the same amount or less than the overall volume of the sample solution. For example, in some embodiments the sample solution may have a total volume of about 100-350 µl while the lower portion 108-A1 may have a volume of about 100-300 µl. In some embodiments, the ratio of the total volume of the sample solution to the volume of the lower portion 108A-1 of the specimen-receiving chamber 108 may be about 1:1 to 4:1.

In some embodiments, the method 200 additionally includes concentrating the sample solution with the analyte. For example, as illustrated in FIG. 3D, a mechanical energy in the form of a rotational energy may be imparted to the swab 300, thereby causing the analyte to be extracted from the wetted swab. The rotation causes the extracted analyte to mix with the buffer solution occupying the lower portion of the specimen-receiving chamber. While the sample solution may be present in excess of the volume of the lower portion 108A-1, due to limited diffusion of the analyte, the specimen-receiving chamber 108 causes a temporarily elevated concentration of the analyte in the sample solution occupying the lower portion 108A-1 of the specimen-receiving chamber 108 relative to the sample solution occupying the upper portion 108A-2 of the specimen-receiving chamber 108.

The sample solution is flowed through the microreactor in a first direction from the specimen-receiving chamber to contact the porous wicking filter and form therein an analyte-capture molecule complex. As illustrated in FIG. 3D, analyte moves from the specimen-receiving chamber 108 to the porous wicking filter 116. The porous wicking filter 116 may comprise a plurality of capture molecules 119 and detection molecules 121. The capture molecules 119 may comprise a binding component 123, such as streptavidin, that allows for the immobilization of the analyte-capture molecule complex at a test line 126 on the absorbent strip pad 124, as illustrated in FIG. 3E. The detection molecules 121 may comprise a detection component 125, such as a colorimetric component, that allows for visualization of the immobilized analyte-capture molecule complex.

It will be appreciated that, while embodiments described herein are implemented using the wetted swab 300 for introducing a sample specimen containing the analyte into the specimen-receiving chamber 108, embodiments are not so limited. In other implementations, the sample specimen may be introduced into the specimen-receiving chamber 108 using other means, e.g., a pipette or directly from a human body.

Still referring to FIG. 2, the method 200 additionally includes causing 212 the sample solution containing the analyte to vertically flow through the reactor chamber 112 of the microreactor 104 to form an analyte-capture molecule complex in the reactor chamber 112. Again, as shown in FIG. 3D, in some embodiments the sample solution containing the analyte flows through the porous wicking filter 116 impregnated with the capture molecule 119, e.g., a capture antibody and, in some embodiments, a detection molecule 121, such as a detection antibody.

In some embodiments the wicking filter may comprise a capture molecule, such as a capture antibody, at a concentration of about 0.1 to 2 mg/ml in the sample solution. In some embodiments the wicking filter may comprise a detection molecule, such as a labelled detection antibody, at a concentration of about 0.001 to 0.1% in the sample solution. The analyte is able to react with the capture molecule in the wicking filter and/or detection molecule, and a sample solution containing the analyte-capture molecule complex is formed. Thus, unlike various methods of using lateral flow assay devices known in the industry, the formation of analyte-capture molecule complex occurs prior to the sample solution reaching the absorbent strip pad 124.

Still referring to FIG. 2, the method 200 further includes causing 216 the sample solution containing the analyte-capture molecule complex to be transferred to an absorbent strip pad. As illustrated in FIG. 3E, the absorbent strip pad 124 is configured to laterally flow the sample solution therethrough, in a second direction crossing the first direction. The analyte-capture molecule complex can then be detected in the absorbent strip pad to identify the presence of the analyte in the sample specimen. In some embodiments the analyte-capture molecule complex is immobilized on a test line 126 on the absorbent strip pad 124. The test line 126 comprises a plurality of binding molecules that are specific for a component of the analyte-capture molecule complex, such as the binding component 123 of the capture molecule 119, and bind to and immobilize the analyte-capture molecule complex on the test line 126. Immobilization of the analyte-capture molecule complex can be visualized, for example with the human eye or with a reader device, and indicates a presence of the analyte-capture molecule complex. In some embodiments the test line 126 may comprise a plurality of binding molecules 126 that are specific for a binding component 123 of the capture molecule 119 and thus are able to bind to and immobilize the analyte-capture molecule complex. For example, the test line 126 may comprise a plurality of streptavidin molecules, which are able to specifically bind a biotin-labeled capture molecule, such as an antibody, and immobilize the analyte-capture molecule complex. As illustrated, the analyte-capture molecule complex also comprises a labeled detection molecule 121, such as a detection antibody 121, and thus the immobilized analyte-capture molecule complex can be visualized.

Referring back to FIG. 1A, the inventors have found that the microreactor 104 provides various advantageous control capabilities as described herein, including a spatial and temporal control of the movement and reaction of the analyte as it is transferred through the microreactor 104 to enhance the sensitivity, efficiency and speed of the analyte detection. These control capabilities arise in part from various structural aspects of the inventive arrangement of the microreactor 104 described herein. FIGS. 4A and 4B schematically illustrate various advantageous arrangements of the microreactor for providing superior detection, according to embodiments.

FIG. 4A illustrates, in particular, various advantages of the microreactor 104 that arise from the proximity between the sample solution containing the analyte to be detected in the specimen-receiving chamber 108 and one or both of the capture molecule, e.g., a capture antibody for forming the analyte-capture molecule complex, and the detection molecule, such as an antibody labeled with a colorimetric component, e.g., a detection antibody. The close proximity is provided by the particular arrangement of the microreactor 104 described herein, which includes the specimen-receiving chamber 108 configured to directly receive the sample specimen, e.g., via a swab 300 wetted with the sample specimen containing the analyte, and the reaction chamber 112 comprising the capture molecule and/or the detection molecule impregnating the porous wicking filter 116. Thus, the analyte comes into direct contact with the capture molecules and the detection molecules immediately upon forming the sample solution from, e.g., a mixture of a sample specimen, e.g., a nasal specimen, and a buffer solution. The inventors have discovered that this proximity is critical because a substantial amount of the analyte, e.g., as much as 80% of the total analyte available in the sample specimen soaking the swab 300 becomes available during initial seconds upon providing the mechanical energy to, e.g., by rotating, the swab 300. As described above, because of the relatively limited volume of the lower portion 108A-1 of the specimen-receiving chamber 108, a lower sample solution 400A formed in the lower portion 108A-1 of the specimen-receiving chamber 108 becomes highly concentrated with the analyte relative to an upper sample solution 400B in the upper portion 108A-2 of the specimen-receiving chamber 108. It will be appreciated that the concentration difference between lower and upper sample solutions 400A and 400B can be temporary, as eventually the higher analyte concentration in the lower sample solution 400A will provide a driving force for diffusion of the analyte towards the upper sample solution 400B to equate the concentration of the analyte in the specimen-receiving chamber 108. As such, having the capture molecule and/or the detection molecule within close proximity to the sample solution 400A for rapid formation of the analyte-capture molecule complex can be critical to enhancing the sensitivity of detection. This close proximity is provided in operation by the porous wicking filter 116 in contact with the sample solution 400A.

Still referring to FIG. 4A, according to embodiments, the reaction between the analyte and one or both of the capture molecule, e.g., capture antibody, and detection molecule can be further enhanced by providing a higher concentration of the capture molecule and/or the detection molecule in the upper portion 116A, e.g., upper half of the porous wicking filter 116. In these embodiments, the porous wicking filter 116 comprises an elongated portion in which the upper portion 116A proximal to the specimen-receiving chamber 108 has a higher concentration of one or both of the capture molecule and/or the dye molecule relative a lower portion 116B proximal to the absorbent strip pad 124. For example, the upper half of the porous wicking filter 116 may have greater than 50%, 60%, 70%, 80%, 90% of the total amount of one or both of the capture molecule and the detection molecule in the porous wicking filter 116, or a value in a range defined by any of these values.

FIG. 4B illustrates various advantages of the vertically arranged microreactor 104 that arise from the reactor chamber 112 including the porous wicking filter 116 in contact with the sample solution containing the analyte, according to embodiments. The physical structure of the porous wicking filter 116 is such that the reaction chamber 112 is configured to facilitate the physical transfer of the sample solution from the specimen-receiving chamber 108 to the absorbent strip 120 (FIG. 1A) at a controlled flow rate. The controlled flow rate in turn provides a targeted residence time of the analyte in the reaction chamber 112. The targeted residence time may be such that, among other advantages, the sensitivity of the diagnostic assay device 100 is enhanced by allowing for increased probability of a reaction between the analyte and the capture molecule to form the analyte-capture molecule complex, and between the analyte-capture molecule complex and the detection molecule. The inventors have found that the attributes of the physical structure of the porous wicking filter 116 that are critical for achieving the high sensitivity of the assay device 100 includes the microstructure of the porous wicking filter 116, the area of the porous wicking filter 116, the length of the porous wicking filter 116 and the volume of the wicking filter 116, as described herein.

The porous wicking filter 116 has a microstructure adapted to control the speed of the sample solution flowing vertically therethrough. As discussed above, in addition to gravity, the porous wicking filter 116 may provide capillary force as an additional driving force for the liquid sample passing therethrough. According to some embodiments, the porous wicking filter 116 may include a suitable microstructure for providing a relatively high surface area for capturing one or both of the capturing molecule and the dye molecule. For example, the suitable microstructure may include a fibrous or sintered particle structure formed of a polymeric material such as polystyrene, polyphenylene sulfide, poly(butylene terephthalate), poly(ethylene terephthalate), polypropylene, polyethylene and polytetrafluoroethylene, to name a few. However, embodiments are not so limited, and the suitable microstructure may be formed of a fibrous or sintered particle structure formed of glass, natural fibers, ceramic, metallic material, carbon, or combinations thereof.

In some embodiments, the wicking filter 116 comprises an irregular fiber structure, to increase incubation time and promote molecular movement, leading to greater interaction between the analyte and the capture and detection molecules. In some embodiments the wicking filter 116 comprises an irregular structure of condensed fibers. In some embodiments the wicking filter 116 comprises an irregular structure of fibers, such as polyester fibers, with a packing density of about 0.35 g/cc.

In some embodiments the wicking filter 116 comprises a regular fiber structure. In some embodiments the wicking filter 116 is formed of fibers arranged parallel to each other. In some embodiments the wicking filter 116 is formed of fibers arranged in a lattice structure.

According to various embodiments, the porous wicking filter 116 may have a porosity, which refers to the open space divided by the macroscopic volume occupied by the porous wicking filter 116, that is less than 0.5, 0.4, 0.3, 0.2, 0.1 or a value in a range defined by any of these values. The porous wicking filter 116 may have a density greater than 0.3 g/cm$^3$, 0.5 g/cm$^3$, 0.7 g/cm$^3$, 0.9 g/cm$^3$, 1.1 g/cm$^3$, or a value in a range defined by any of these values, for instance about 0.3-1.0 g/cm$^3$. In addition, the porous wicking filter 116 may have an average pore size that is greater than about 10 μm, 50 ρ, m, 100 μm, 150 ρ, m, 200 μm, 250 ρ, m or a value in a range defined by any of these values, for instance about 10-100 ρ, m.

In some embodiments the porous wicking filter 116 is able to accommodate a volume or sample solution that is equal to or less than the volume of the lower portion 108A-1 of the specimen-receiving chamber. For example, in some embodiments the capacity of the porous wicking filter may be about 100 μl while the volume of the lower portion 108A-1 of the specimen-receiving chamber may be about 100-300 μl. In some embodiments, the ratio of the total volume of the porous wicking filter 116 to the volume of the lower portion 108A-1 of the specimen-receiving chamber 108 may be about 1:1 to 1:3. The ratio of the total volume of the porous wicking filter 116 to the total sample volume may be from about 1:1 to 1:4 in some embodiments.

In addition to the microstructure, the cross-sectional area and the length of the porous wicking filter 116 in the vertical flow direction may have values adapted to provide a targeted residence time of the sample solution flowing therethrough. For example, for the cylindrical shape of the wicking filter 116 illustrated in FIG. 1A, the diameter D (FIG. 4B) is directly proportional to the flow rate, and the length L is directly proportional to the residence time of the sample solution.

Still referring to FIG. 4B, the porous wicking filter 116 is critically designed such that a high fraction of the analyte contained in the lower sample solution 400A (FIG. 4A) forms the analyte-capture molecule complex during a targeted residence time in the porous wicking filter 116, prior to being transmitted to the absorbent strip pad below. This is because, as described above, the lower sample solution 400A in the lower portion 108A-1 of the specimen-receiving chamber 108 is highly concentrated with the analyte relative to the upper sample solution 400B in the upper portion 108A-2 of the specimen-receiving chamber 108. For example, the dimensions and microstructure of the porous wicking filter 116 may be designed such that it holds a sample volume equal to or less than 100% of the volume of the lower sample solution 400A. For example, in some embodiments a sample solution may have an overall volume of about 100-350 μl, while the lower portion 108A-1 of the specimen-receiving chamber 108 has a volume of about 100-300 μl and the porous wicking filter 116 is configured to hold a maximum volume of about 100 μl. However, in some embodiments the dimension and microstructure of the porous wicking filter 116 may be such that it holds greater than 100%, 200%, 300%, 400%, 500% of the volume of the lower sample solution 400A, or a value in a range defined by any of these values. Thus configured, the targeted residence time of the highly concentrated lower sample solution 400A can be designed to be greater than 10 sec, 30 sec, 1 min, 10 min, 30 min., 50 min, or value in a range defined by any of these values.

Figure 4C:
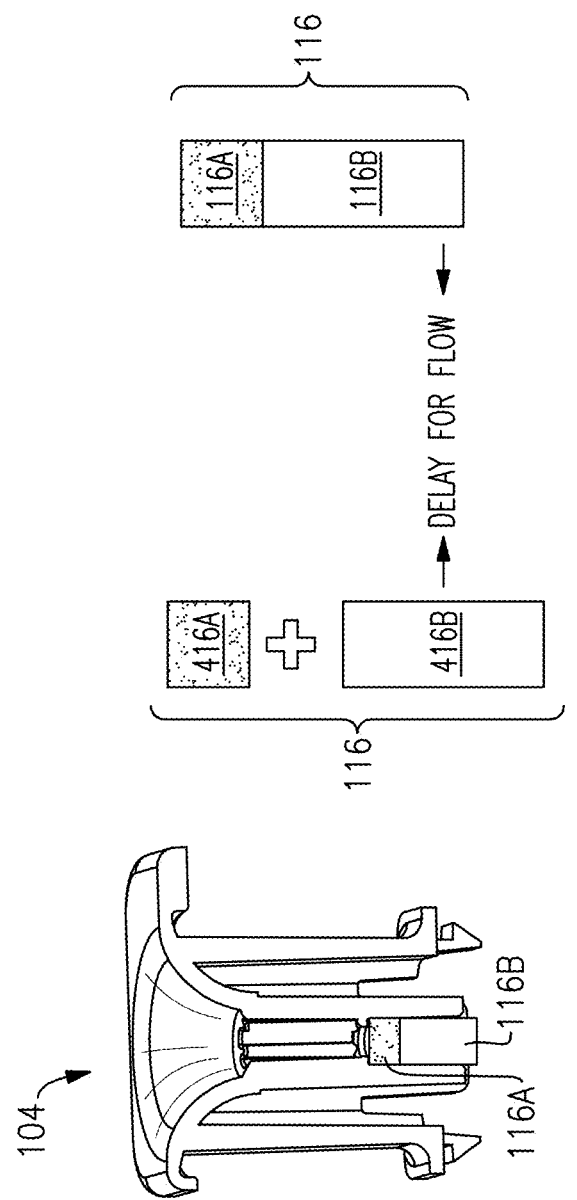
FIG. 4C schematically illustrates advantageous arrangements of a wicking filter in a microreactor of a diagnostic assay device, according to embodiments.

FIG. 4C schematically illustrates advantageous arrangements of a wicking filter in a microreactor of a diagnostic assay device, according to embodiments. As illustrated above with respect to FIG. 4A, it may be advantageous to divide the porous wicking filter 116 into an upper portion 116A having a relatively higher concentration of the capture molecule and/or the dye molecule and a lower portion 116B having a relatively lower concentration of the capture molecule and/or the dye molecule. The upper portion 116A is proximal to the specimen-receiving chamber 108 has a higher concentration of one or both of the capture molecule and/or the detection molecule relative the lower portion 116B proximal to the absorbent strip pad 124.

The upper portion 116A of the porous wicking filter 116 may serve, among functions, the function of providing highly concentrated capture molecules for reacting with highly concentrated analyte in the lower sample solution 400A (FIG. 4A) as provided in the lower portion 108A-1 of the specimen-receiving chamber 108, as described above with respect to FIGS. 4A and 4B. By providing the highly concentrated capture molecules commensurate with the highly concentrated analyte, the relative amounts of the analyte and capture molecules that are mutually available for forming the analyte-capture molecule are increased, while reducing the relative amounts of unused analyte and/or capture molecules. Further, by disposing the highly concentrated analyte and highly concentrated capture molecules in close proximity to one another, the time it takes for the sample specimen containing the analyte to pass through the area containing the capture molecules is reduced, while simultaneously increasing the spatial overlap of high concentration regions of concentration profiles of the analyte and the capture molecules. Similarly, the upper portion 116A of the porous wicking filter 116 may serve to provide highly concentrated detection molecules for reacting with the analyte and/or the analyte-capture molecule complex. According to embodiments, the bulk of the analyte-capture molecule complex is formed within the upper portion 116A of the wicking filter 116. The upper portion 116A of the porous wicking filter 116 may also serve a filter function, removing undesirable material, such as mucus, from the sample.

The lower portion 116B of the porous wicking filter 116 may serve, among other functions, to delay the transfer of the sample solution to the absorbent strip pad 124 (FIG. 1A) for laterally flowing the sample solution containing the antigen-capture molecule complex for visual detection. In some implementations, while the bulk of the analyte-capture molecule complex is formed within the upper portion 116A, the sample solution may carry remaining portions of the analyte and the capture molecules that have not reacted with each other. In these implementations, the lower portion 116B may provide the time needed for the remaining portions of the analyte and the capture molecules and detection molecules to further form the analyte-capture molecule complex.

In some embodiments the lower portion 116A of the porous wicking filter may serve to provide highly concentrated capture molecules and/or detection molecules, while the upper portion 116B may serve to delay the transfer of sample solution, providing additional time for the analyte and capture and detection molecules to form the analyte-capture molecule complex in the lower portion 116A.

In some embodiments, the porous wicking filter 116 may be a single piece article having the upper and lower portions 116A, 116B. In some other embodiments, the porous wicking filter 116 may be formed of two discrete pieces, including the upper and lower portions 416A, 416B. As described below with respect to FIGS. 9A-10B, the relative vertical position of the high capture molecule concentration region and/or the high detection molecule concentration region can significantly affect the resulting sensitivities.

FIG. 5 schematically illustrates, in operation, a diagnostic device having a microreactor configured for indication of a presence of the analyte-capture molecule complex, according to embodiments. In particular, FIG. 5 illustrates the mechanism for the detection of an analyte-capture molecule complex using, without limitation, SARS-CoV-2 antigen detection as an example. As described above (e.g., with respect to FIG. 4A), a sample specimen 504 containing an analyte, e.g., a SARS-CoV-2 antigen 524, is received by the specimen-receiving chamber 108 of the microreactor 104, where it is mixed with a buffer solution to form a sample solution containing the SARS-CoV-2 antigen 524 suspended in the buffer solution. The sample solution having the SARS-CoV-2 antigen 524 suspended therein is transferred to the reaction chamber 112 of the microreactor and flows through the porous wicking filter 116 disposed in the reaction chamber 112 as described above (e.g., with respect to FIG. 4B). The SARS-CoV-2 antigen 524 comes into proximity of one or more capture molecules and detection molecules. The one or more capture molecules and detection molecules can include, e.g., a capture antibody and a detection antibody. For example, in the illustrated example, the SARS-CoV-2-specific antibodies 512, 520 can be detection and capture antibodies, respectively. The antigen 524 and the antibodies 512, 520 form an antigen—antibody complex 514. In the illustrated example, the one or more SARS-CoV-2-specific antibodies 512, 520 includes blue CNB-conjugated anti-SARS-CoV-2 antibody (detection molecule 512) and biotin-conjugated anti-SARS-CoV-2 antibody (capture molecule 520), respectively, and the antigen-capture molecule complex 514 is an antibody-antigen-capture molecule complex. Thus, formed antigen-capture molecule complex 514 migrates vertically via gravity and capillary action through the porous wicking filter 116, and subsequently laterally across the absorbent strip pad 124. Also released from the porous wicking filter 116 as the sample solution passes therethrough is a control capture molecule 508 conjugated to a detectible tag, such as a colorimetric tag. The control capture molecule is configured such that it does not bind to the analyte of interest and is not bound by binding molecule 516. The control capture molecule 508 includes a detection component, such as a colorimetric component or tag, to allow for its visualization at a test line. In the illustrated example, the control capture molecule 508 comprises a colloidal gold-conjugated chicken Ig Y antibody. Thus, formed sample solution containing the antigen-capture molecule complex 514, the conjugated control capture molecule 508 and unreacted antigen 524 and antibodies 512, 520 are transferred vertically from the porous wicking filter 116 to the absorbent strip pad 124 in contact therewith.

Still referring to FIG. 5, the absorbent strip pad 124 is configured to receive and laterally flow the sample solution containing the antigen-capture molecule complex 514. The absorbent strip pad 124 receives the sample solution through an absorbent pad 540 connected to a filter pad 544 and a nitrocellulose membrane 548. The nitrocellulose membrane has bound thereon, at a test line 532, a binding molecule 516, such as a binding protein. The binding molecule 516 has a high affinity to the antigen-capture molecule complex 514, and effectively immobilizes the antigen-capture molecule complex 514 for visual detection thereof. In the illustrated example, the binding molecule 516 is streptavidin, which has a high affinity to biotin of the biotin-conjugated anti-SARS-CoV-2 antibody 520. The nitrocellulose membrane further has formed thereon, at a control line 536, a control binding molecule 528. In the illustrated example, the control binding molecule 528 is anti-chicken IgY antibody, which effectively immobilizes the control capture molecule 508, which again is a colloidal gold-conjugated chicken Ig Y antibody. Thus configured, the antigen 524, when present above a minimum detection level, can be visually detected at the test line 532 through the binding of the antigen-capture molecule complex 508 to the binding molecule 516, and the control capture molecule 508 can be visually detected at the control line 536 through the binding of the control capture molecule 508 to the control binding molecule 528.

The rapid diagnostic test method employed by the diagnostic device as described above with respect to FIG. 5 may be referred to in the industry as a sandwich type assay. However, it will be appreciated that the type of assays the diagnostic devices described herein can be configured for are not limited thereto. Without limitation, the diagnostic devices described herein can be configured for various types of assay methods including sandwich, competitive, enzymatic, direct, indirect, fluorescence and chemiluminescence methods, to name a few.

Figure 6:
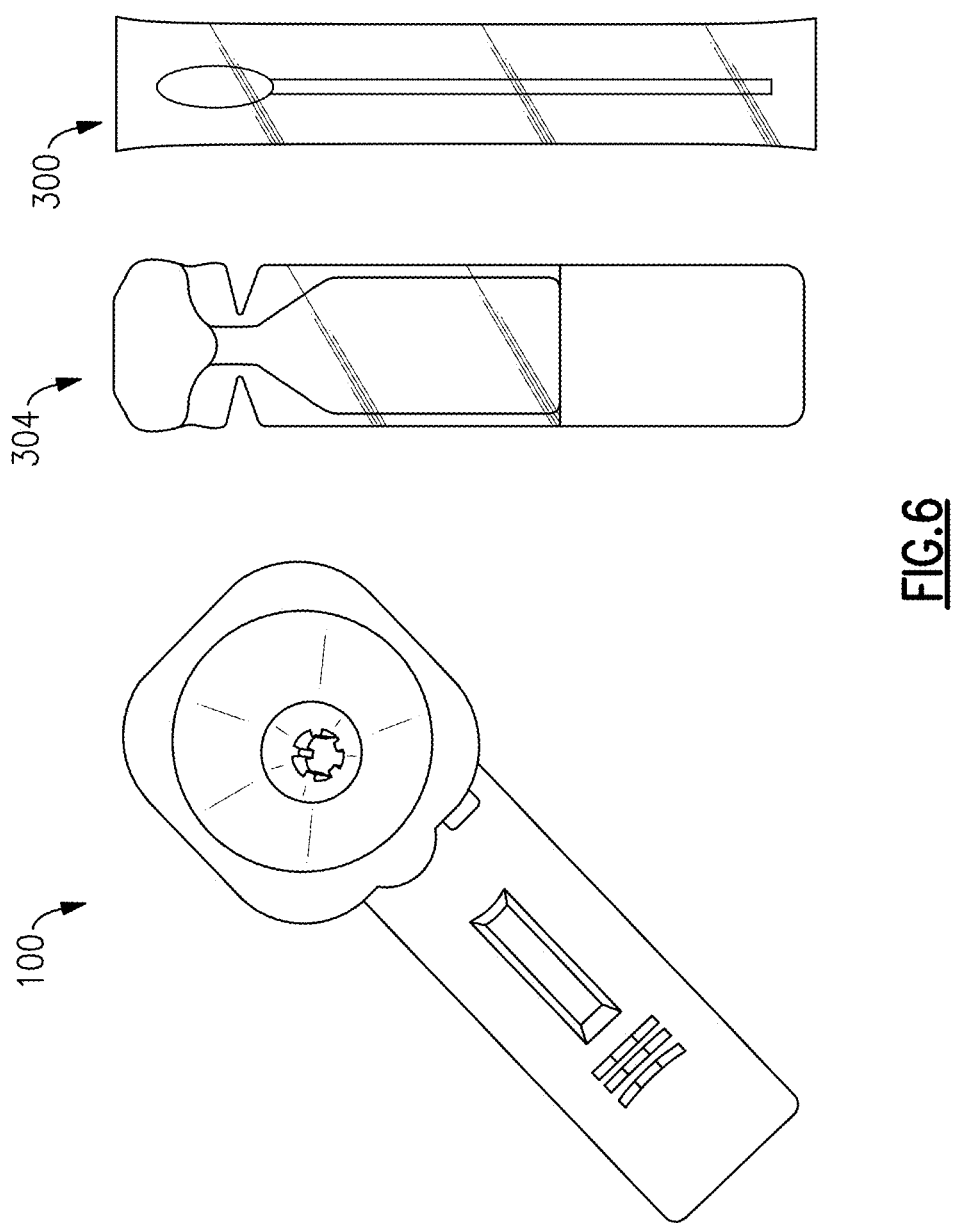
FIG. 6 illustrates a diagnostic assay kit for detecting an analyte in a sample solution including a diagnostic assay device comprising a microreactor, according to embodiments.

FIG. 6 illustrates a diagnostic assay kit for detecting an analyte in a sample solution, according to embodiments. The diagnostic assay kit includes a swab 300 configured to be wetted with a sample specimen containing the analyte. The assay kit additionally comprises a diagnostic assay device 100 comprising a microreactor configured to form a sample solution containing the analyte and vertically flow the sample solution therethrough to form an analyte-capture molecule complex. The microreactor is configured to transfer the sample solution to an absorbent strip pad configured to laterally flow therethrough the sample solution including the analyte-capture molecule complex formed in the microreactor and indicate a presence of the analyte-capture molecule complex. The assay kit further comprises a buffer solution 304 configured to be mixed with the sample specimen to form the sample solution in the microreactor. The kit can be used to, e.g., implement the method described above with respect to FIG. 2.

TABLES 1 and 2 illustrate experimental comparisons of the detection capabilities between a diagnostic assay device ("Example Covid19 Antigen Home Test") comprising a microreactor according to embodiments and a control diagnostic assay device without such a microreactor ("Comparative Covid 19 Antigen Home Test"). Unlike the diagnostic assay device according to embodiments in which the capture antibodies and detection molecules are present in a microreactor the control diagnostic assay device is a lateral flow assay without such vertical microreactor, in which the capture antibodies and the detection molecules are present in a lateral flow absorbent strip pad. The measurements were performed using inactivated SARS-CoV-2 virus. ABLE 1 tabulates the detected amounts of the inactivated virus, while TABLE 2 tabulates the dilution factor. The results indicate that the limit of detection can be as low as 175 $TCID_{50}$/ml) for the assay device comprising a vertical flow microreactor according to embodiments, which is an improvement of over 8× compared to the control device.

TABLE 1

| Number of Inactivated Virus ($TCID_{50}$/ml) | Comparative Example Covid19 Antigen Home Test | Example Covid19 Antigen Home Test |
| --- | --- | --- |
| 5600 | + | +++ |
| 2800 | + | +++ |
| 1400 | − | +++ |
| 700 | − | +++ |
| 350 | − | ++ |
| 175 | − | + |
| 87.5 | − | +/− |
| 43.75 | − | − |
| 21.875 | − | − |
| 0 | − | − |

TABLE 2

| Clinical Specimen (Dilution factor) | Comparative Example Covid19 Antigen Home Test | Example Covid19 antigen Home Test |
| --- | --- | --- |
| 1 | +++ | +++ |
| 2 | +++ | +++ |
| 4 | +++ | +++ |
| 8 | +++ | +++ |
| 16 | + | +++ |
| 32 | +/− | +++ |
| 64 | − | +++ |
| 128 | − | +++ |
| 256 | − | + |
| 512 | − | + |

Figure 7:
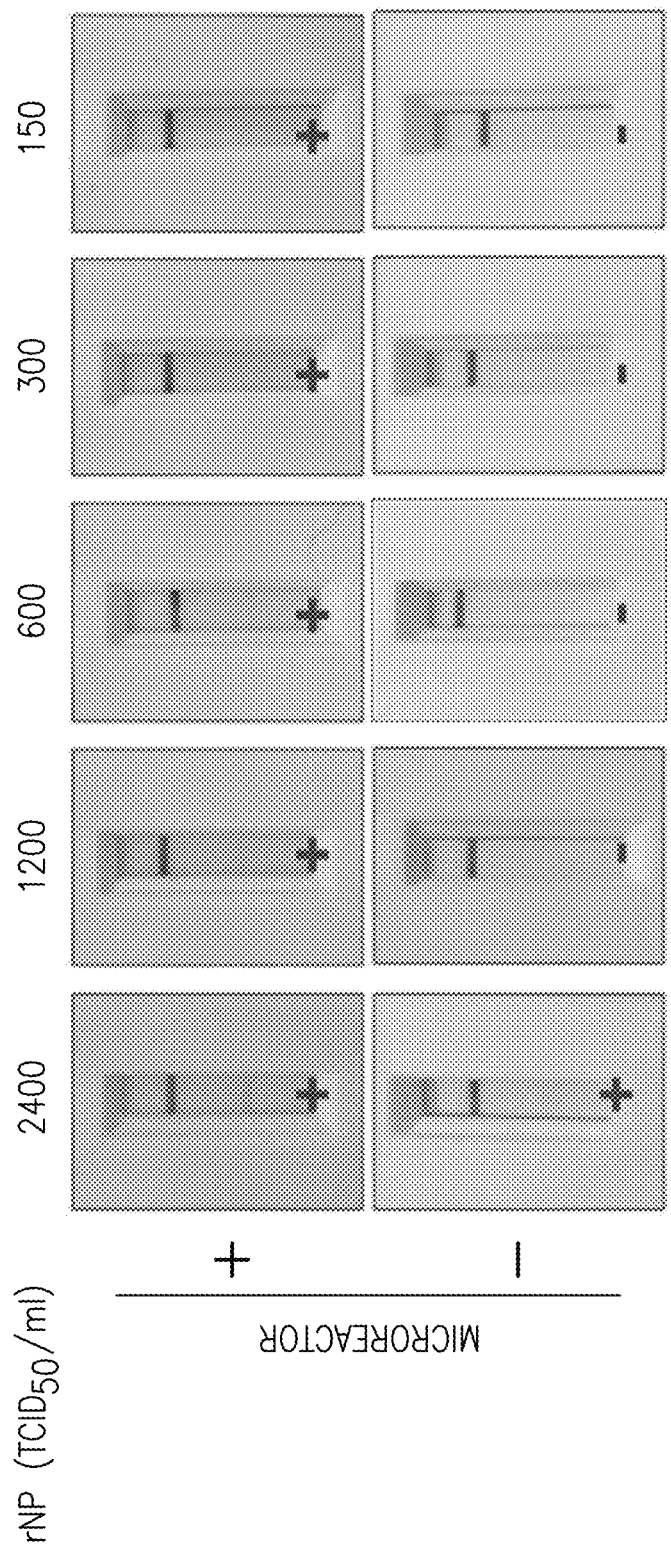
FIG. 7 illustrates a visual experimental comparison between a diagnostic assay device comprising a microreactor according to embodiments, and a control diagnostic assay device without a microreactor.

FIG. 7 illustrates a visual experimental comparison between a diagnostic assay device comprising a microreactor according to embodiments, and a control diagnostic assay device without such a microreactor. The experimental comparison is that of the devices similar to those compared above with respect to TABLES 1 and 2. In a similar manner as described with respect to the experimental results shown in TABLES 1 and 2, the measurements were performed using inactivated SARS-CoV-2 virus. The comparison was made using 12 μl of the sample specimen within varying amounts of inactivated virus. The upper row of photographs are those of the viewing windows of the diagnostic assay devices comprising a vertical flow microreactor, having introduced therein varying amounts of the inactivated virus. The lower row of photographs are those of the viewing windows of the control diagnostic assay devices without the microreactor, having introduced therein varying amounts of the inactivated virus. While it may not be readily apparent in the illustrated photographs, the inventors have clearly observed the presence of both the control and test lines in the upper row of photographs corresponding to example assay devices loaded with inactivated virus content as low as 150 $TCID_{50}$/ml. On the other hand, the inventors have only observed the presence of both the control and test lines in the lower row of photographs corresponding to control assay devices loaded with inactivated virus content starting with 2400 $TCID_{50}$/ml. The results indicate that the sensitivity of the example devices may have been improved by as much as sixteen (16) times due to the arrangement in the example assay devices including microreactors, as described above.

Similar to the experiments described above in TABLES 1 and 2 and FIG. 7, FIGS. 8A-8D illustrate experiments comparing the diagnostic sensitivity of a diagnostic device comprising a microreactor as described herein ("Reactor Assay") and a control diagnostic device without such a microreactor ("Standard Assay"). The presence of the microreactor was the only difference in experimental conditions. In all experiments, 2-fold serially diluted samples of the analyte were prepared by dilution of stock solutions in phosphate buffered saline. 50 μL of the diluted sample was applied to a swab and the swab was inserted into the sample port of the reactor or into a vial of extraction buffer. For the device utilizing the reactor as described herein, buffer solution was added to the sample port. For the standard lateral flow assay, the swab was rotated vigorously, removed, and three drops of sample were added to the sample well. Signal intensity was read after 10 minutes using a, WEAK lateral flow reader (iUL, Barcelona, Spain). The same capture and detection antibodies were utilized in each set of assays.

Figure 8A:
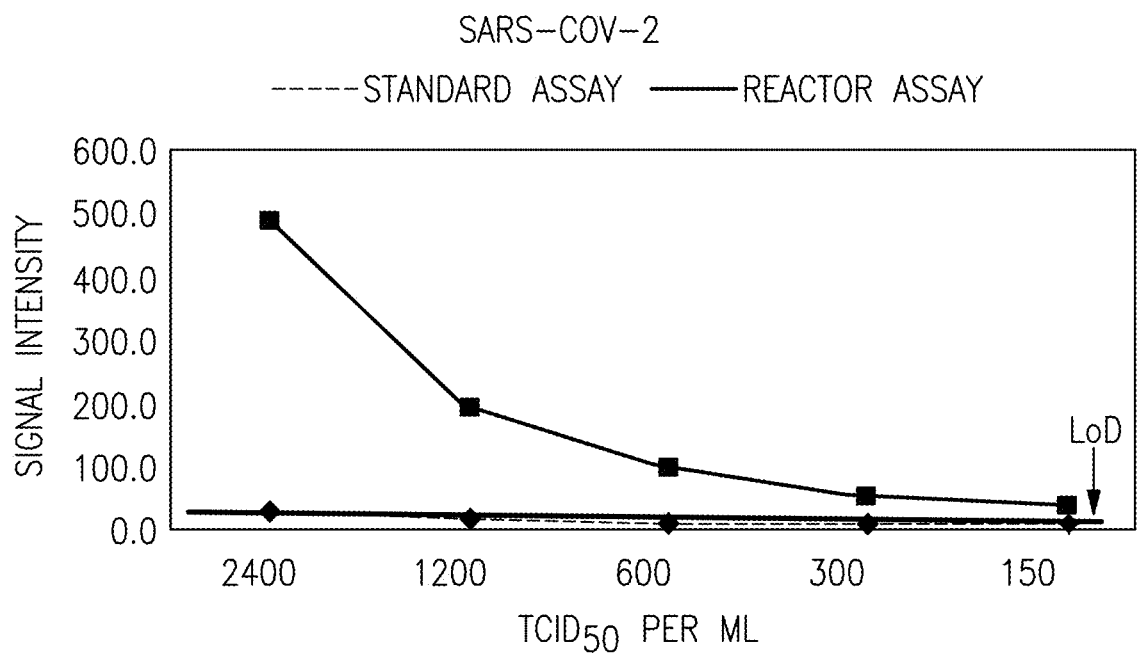
FIGS. 8A-8D illustrate the diagnostic sensitivity of a diagnostic assay device comprising a microreactor as described herein ("Reactor Assay") compared to a control diagnostic device without such a microreactor ("Standard Assay") for a number of different analytes.

As shown in FIG. 8A, for SARS-COV2, the Reactor Assay has a 16-fold higher sensitivity than the Standard Assay when using the same capture and detection antibodies to detect SARS-COV2. The Reactor Assay has a 10-fold higher signal intensity at 1200 $TCID_{50}$ per ml (the detection limit for the Standard Assay).

Figure 8B:
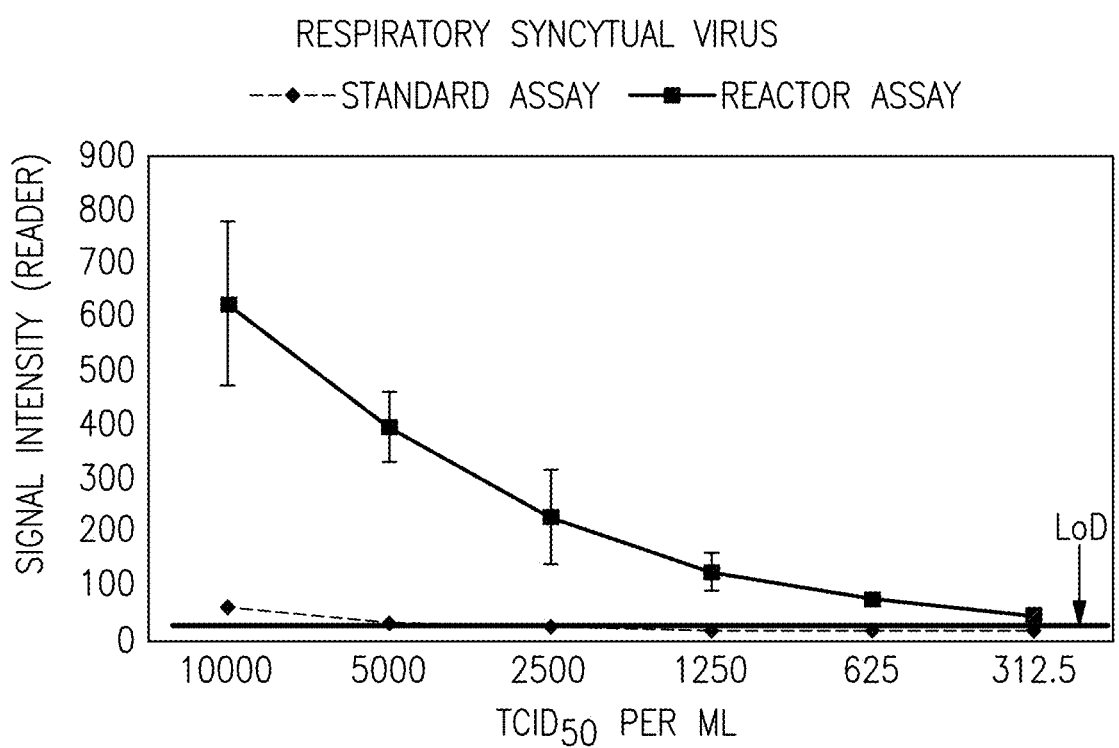

As shown in FIG. 8B, for Respiratory Syncytial Virus, the Reactor Assay has an 8-fold higher sensitivity than the Standard Assay when using the same capture and detection antibodies to detect RSV. The Reactor Assay has a 10-fold higher signal intensity at 5000 $TCID_{50}$ per ml (the detection limit for the Standard Assay).

Figure 8C:
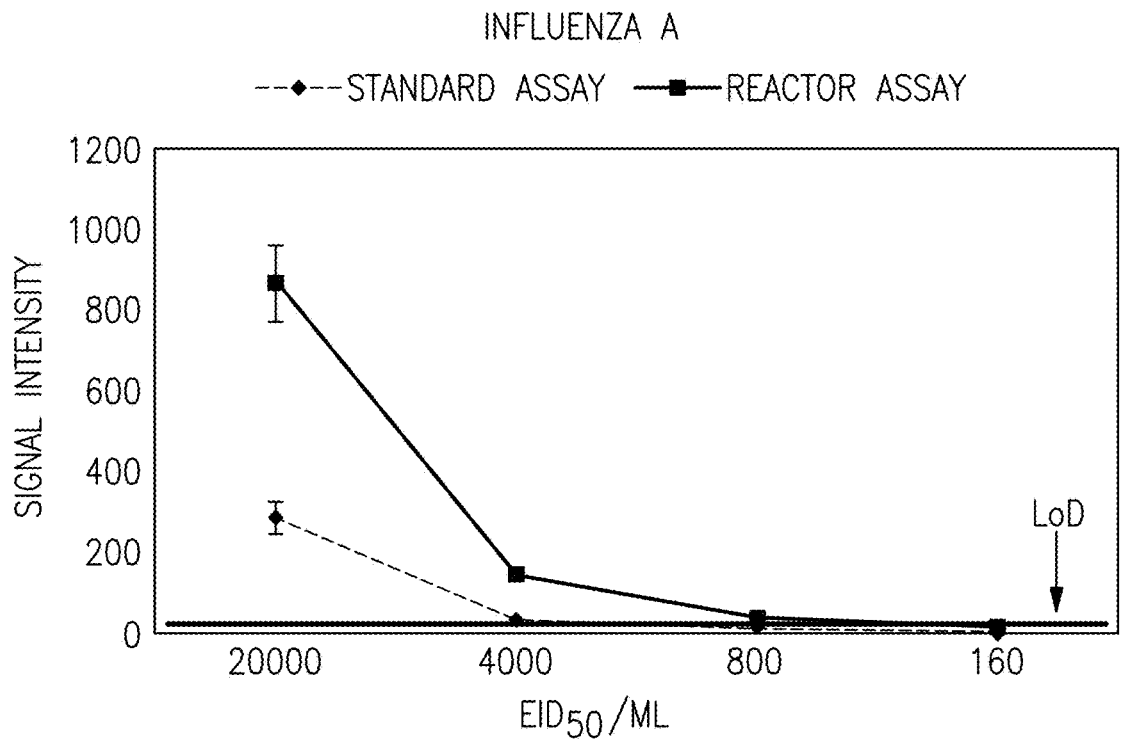

As shown in FIG. 8C, for Influenza A, the Reactor Assay has a 5-fold higher sensitivity than the Standard Assay when using the same capture and detection antibodies to detect Influenza A. The Reactor Assay has a 4-fold higher signal intensity at 4000 $EID_{50}$ per ml (the detection limit for the Standard Assay).

Figure 8D:
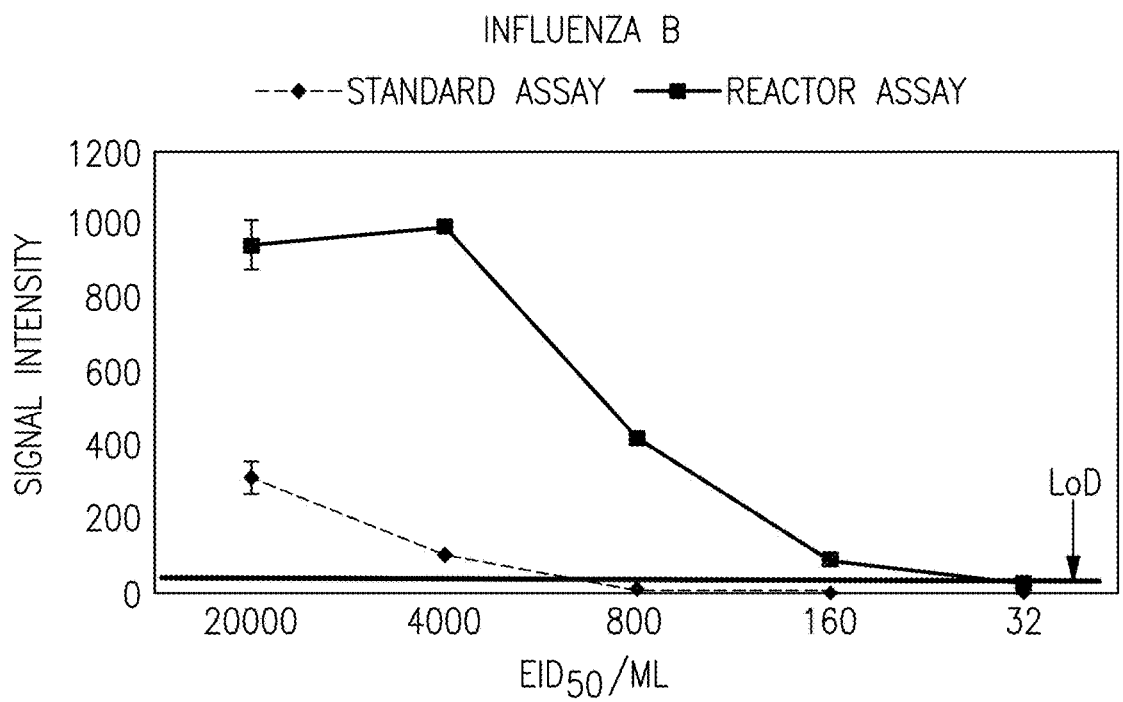

As shown in FIG. 8D, for Influenza B, the Reactor Assay has a 10-fold higher sensitivity than the Standard Assay when using the same capture and detection antibodies to detect Influenza. B. The Reactor Assay has a 10-fold higher signal intensity at 4000 $EID_{50}$ per ml (the detection limit for the Standard Assay).

As described above with respect to FIGS. 4A-4C, the relative position of the capture molecules and/or dye molecules within the wicking filter 116 can significantly affect the resulting sensitivities of the assay devices. FIGS. 9A and 9B, 10A and 10B, 11A and 11B illustrate experimental arrangements and measured sensitivities of diagnostic assay devices having wicking filters arranged to have portions containing relatively high capture molecule concentration and/or relatively high dye molecule concentration at different vertical positions of the microreactors.

Figure 9B:
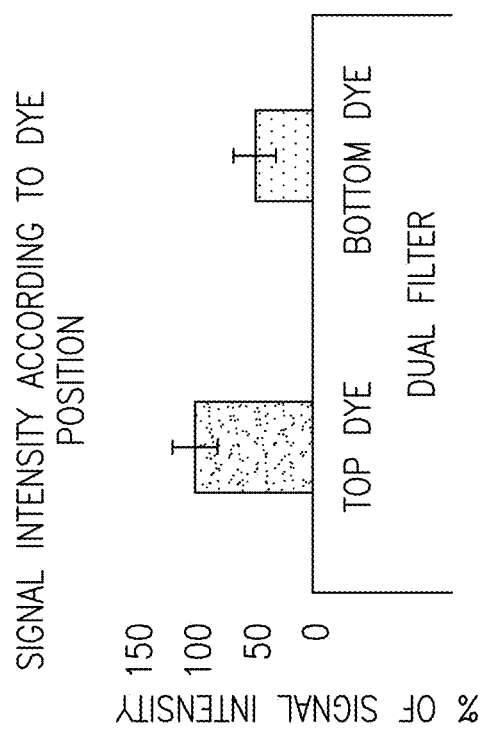
FIGS. 9A and 9B illustrate experimental arrangements and signal intensities measured from diagnostic assay devices having wicking filters arranged to have portions containing relatively high capture molecule concentration and/or relatively high dye molecule concentration at different vertical positions within the microreactors.
Figure 9A:
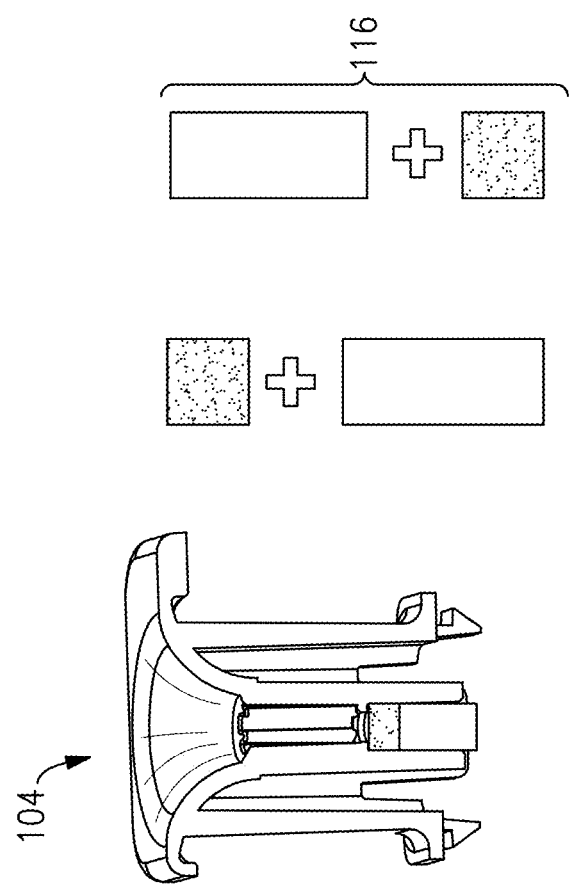

For the comparison of readings of assay devices illustrated in FIGS. 9A and 9B, the porous wicking filters 116 were formed of two discrete pieces, including the upper and lower portions 416A, 416B (FIG. 4C). The experimental comparison is that of devices loaded with inactivated SARS-CoV-2 virus. As shown in FIG. 9A, two samples were tested: a top-concentrated wicking filter (left) and a bottom-concentrated wicking filter (right) having 3 mm concentrated regions (of 9.5 mm total) impregnated with the capture molecules and detection molecules, and 6.5 mm delay regions that are initially free of the capture molecules and dye molecules. As shown in FIG. 9B, the relative signal intensity of the test line, as measured using an optical reader, of the top-concentrated wicking filter is substantially higher relative to that of the bottom-concentrated wicking filter.

Figure 10B:
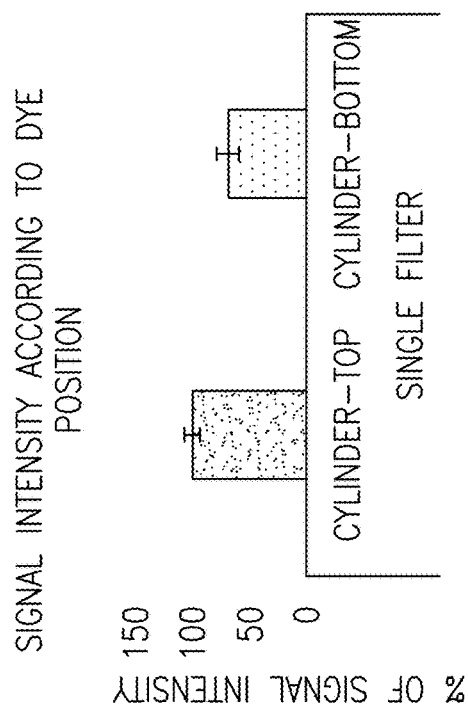
FIGS. 10A and 10B illustrate experimental arrangements and signal intensities measured from diagnostic assay devices having wicking filters arranged to have portions containing relatively high capture molecule concentration and/or relatively high dye molecule concentration at different vertical positions of the microreactors.
Figure 10A:
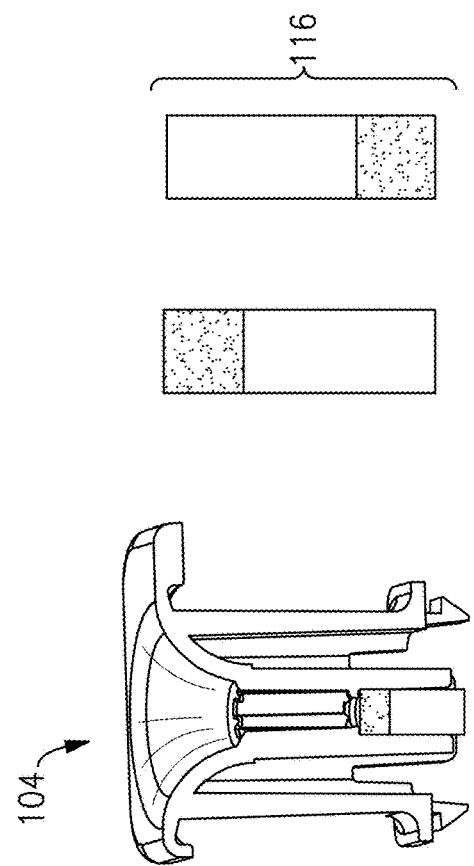

For the comparison of readings of assay devices illustrated in FIGS. 10A and 10B, the porous wicking filters 116 were similar to those tested for the comparison in FIGS. 9A and 9B, except that the porous wicking filters are formed of a single piece, including the upper and lower portions 116A, 116B (FIG. 4C). As shown in FIG. 10A, two samples were tested: a top-concentrated wicking filter (left) and a bottom-concentrated wicking filter (right) having 3 mm concentrated regions (of 9.5 mm total) impregnated with the capture molecules and detection molecules, and 6.5 mm delay regions that are initially free of the capture molecules and detection molecules. As shown in FIG. 9B, the relative signal intensity of the test line, as measured using an optical reader, of the top-concentrated wicking filter is substantially higher relative to that of the bottom-concentrated wicking filter.

Figure 11B:
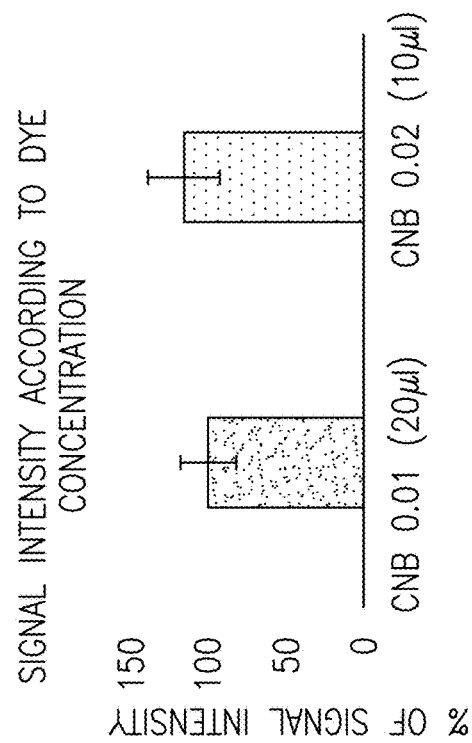
FIGS. 11A and 11B illustrate experimental arrangements and signal intensities measured from diagnostic assay devices having wicking filters arranged to have portions containing relatively high capture molecule concentration and/or relatively high dye molecule concentration at different vertical positions of the microreactors.
Figure 11A:
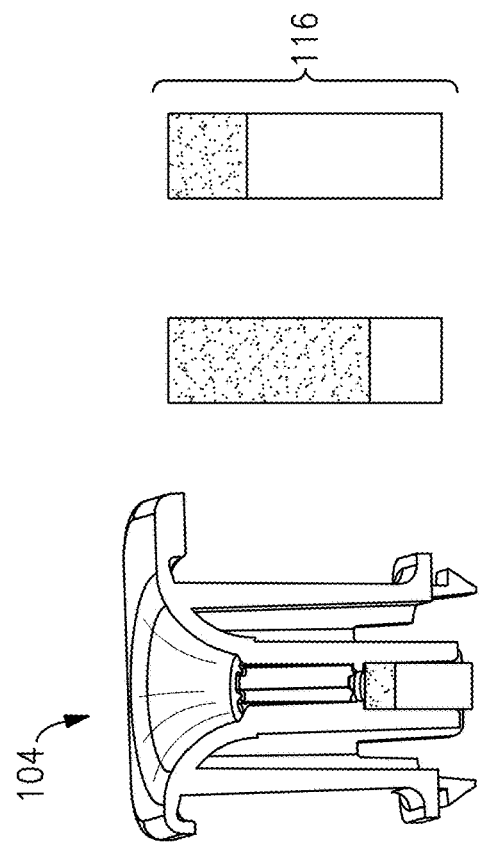

For the comparison of readings of assay devices illustrated in FIGS. 11A and 11B, the porous wicking filters 116 were formed of a single piece, including the upper and lower portions 116A, 116B (FIG. 4C). As shown in FIG. 11A, two top-concentration samples were tested: a top-concentrated wicking filter having a relatively lower concentration over a greater volume (e.g., about 6 mm of 9 mm total) of the wicking filter 116 (left), and a top-concentrated wicking filter having a relatively higher concentration over a smaller volume (e.g., about 3 mm of 9 mm total) of the wicking filter 116 (right), and 6.5 mm delay regions that are initially free of the capture molecules and detection molecules. The absolute amount of the analyte in the two devices were the same. As shown in FIG. 11B, for the same amount of the analyte, relative signal intensity of the test line, as measured using an optical reader, of the top-concentrated wicking filter having a higher concentration over a smaller volume is higher relative to that of the top-concentrated wicking filter having a lower concentration over a larger volume.

The experimental results of FIGS. 9A-11B illustrate that, for enhanced intensity, a top-concentrated wicking filter having a relatively high concentration of the capture molecule/detection molecule closer to the specimen-receiving chamber 108 of the microreactor 104 can be particularly advantageous.

Additional Arrangements

Arrangement 1: A diagnostic assay device for detecting an analyte in a sample specimen, the device comprising a microreactor comprising a specimen-receiving chamber vertically above and fluidly connected to a reaction chamber, the reaction chamber having a cylindrical volume housing a porous wicking filter, the porous wicking filter comprising a plurality of capture molecules adapted to specifically bind to the analyte in the sample solution and form an analyte-capture molecule complex; and an absorbent strip pad that is in contact with the porous wicking filter, wherein the microreactor is configured to receive a sample specimen containing the analyte and a buffer solution in the specimen-receiving chamber to form a sample solution and flow the sample solution in a first direction to contact the porous wicking filter in the reaction chamber and form therein the analyte-capture molecule complex, and to transfer the sample solution containing the analyte-capture molecule complex to the absorbent strip pad, and wherein the absorbent strip pad is configured to flow therethrough, in a second direction crossing the first direction, the sample solution including the analyte-capture molecule complex and indicate a presence of the analyte-capture molecule complex.

Arrangement 2: The device of Arrangement 1, wherein the specimen-receiving chamber comprises an upper portion having a wide top opening adapted to receive a sample specimen comprising the analyte, and a lower portion comprising a cylindrical cavity and a bottom opening adjacent to the reaction chamber, wherein the upper portion is wider than the lower portion and the bottom opening has a diameter narrower than the diameter of the cylindrical cavity.

Arrangement 3: The device of Arrangement 1, wherein the specimen-receiving chamber has a funnel shape, and the lower portion is configured to hold a limited volume of the sample solution and the upper portion configured to hold an excess volume of the sample solution in excess of the limited volume.

Arrangement 4: The device of any one of Arrangements 2-3, wherein the lower portion of the specimen-receiving chamber has a volume of 100-300 µl.

Arrangement 5: The device of any of Arrangements 1-4, wherein the specimen-receiving chamber is configured to receive and extract the sample specimen from a swab comprising the sample specimen.

Arrangement 6: The device of Arrangement 5, wherein the lower portion of the specimen-receiving chamber is configured to stop and hold a swab inserted into the specimen-receiving region.

Arrangement 7: The device of any one of Arrangements 1-6, wherein the reaction chamber is configured to receive the sample solution from the specimen-receiving region and transfer the sample solution to the absorbent strip pad in part using gravity.

Arrangement 8: The device of any one of Arrangements 1-7, wherein the porous wicking filter is configured to contact the sample solution at an upper end thereof and contact the absorbent strip pad at a lower end thereof.

Arrangement 9: The device of any one of Arrangements 1-8, wherein the porous wicking filter additionally comprises a plurality of detection molecules comprising a colorimetric component and adapted to specifically bind to the analyte and/or the analyte-capture molecule complex.

Arrangement 10: The device of Arrangement 9, wherein the porous wicking filter comprises detection molecules at a concentration of about 0.001 to 0.1% in the sample solution.

Arrangement 11: The method of Arrangement 9, wherein the colorimetric component is a dye.

Arrangement 12: The method of Arrangement 9, wherein the colorimetric component is one or more of a cellulose nano bead, colloidal gold, a gold nano shell or a latex bead.

Arrangement 13: The device of any one of Arrangements 1-12, wherein the absorbent strip pad is configured to receive the sample solution from the reaction chamber and transfer the sample solution in a lateral direction to cause a visual indication of a presence of the analyte-capture molecule complex.

Arrangement 14: The device of Arrangement 13, wherein the absorbent strip pad comprises a test line, the test line comprising a plurality of binding molecules adapted to bind the analyte-capture molecule complex.

Arrangement 15: The device of any one of Arrangements 9-14, wherein the porous wicking filter comprises an elongated portion in which an upper portion proximal to the specimen-receiving chamber has a higher concentration of one or both of the capture molecules or detection molecules relative to a lower portion proximal to the absorbent strip pad.

Arrangement 16: The device of Arrangement 15, wherein the entire concentrations of one or both of capture molecules and/or detection molecules are confined within an upper 50% of a length of the porous wicking filter.

Arrangement 17: The device of any one of Arrangements 9-16, wherein the porous wicking filter comprises an elongated portion in which an upper portion proximal to the specimen-receiving chamber has one or both of the capture molecules or detection molecules while a lower portion proximal to the absorbent strip pad is free of one or both of the capture molecules or dye molecules.

Arrangement 18: The device of any one of Arrangements 1-17, wherein the porous wicking filter has a microstructure including porosity such that the reaction region is configured to transfer the sample solution from the specimen-receiving region to the absorbent strip pad in part by capillary action in addition to gravity.

Arrangement 19: The device of any one of Arrangements 1-18, wherein the porous wicking filter comprises a porous polymeric material.

Arrangement 20: The device of any one of Arrangements 1-19, wherein the porous wicking filter comprises an irregular structure of fibers with a packing density of about 0.35 g/cc.

Arrangement 21: The device of any one of Arrangements 1-20, wherein the porous wicking filter is impregnated with the capture molecule.

Arrangement 22: The device of any of Arrangements 1-21, wherein the absorbent strip pad is configured to transfer the sample solution in the second direction substantially by capillary action.

Arrangement 23: The device of any of Arrangements 1-22, wherein the absorbent strip pad is substantially free of the capture molecules.

Arrangement 24: The device of any one of Arrangements 9-23, wherein the absorbent strip pad is substantially free of the detection molecules.

Arrangement 25: The device of any one of Arrangements 1-24, wherein the porous wicking filter has dimensions and porosity configured for a controlled flow rate, such that a time duration corresponding to the passage of the limited volume of the sample solution from the lower portion of the specimen-receiving chamber through the reaction chamber corresponds to a reaction time for substantial formation of the analyte-capture molecule complex.

Arrangement 26: The device of any one of Arrangements 1-25, wherein the porous wicking filter comprises capture molecules at a concentration of 0.1 to 2 mg/ml in the sample solution.

Arrangement 27: The device of any one of Arrangements 1-26, wherein the capture molecule is an antibody.

Arrangement 28: The device of any one of Arrangements 1-27, wherein the analyte is an antigen.

Arrangement 29: The device of Arrangement 28, wherein the antigen is a SARS-CoV-2, RSV, influenza A or influenza B antigen.

Arrangement 30: The device of Arrangement 29, wherein the capture molecule is a SARS-CoV-2, RSV, influenza A or influenza B antibody.

Arrangement 31: The device of any one of the above Arrangements, wherein the first direction is a vertical direction within an angle of about 45° with respect to the direction of the direction of the force of gravity.

Arrangement 32: The device of any of the above Arrangements, wherein the first direction is a vertical direction substantially parallel to a direction of the force of gravity.

Arrangement 33: The device of any one of the above Arrangements, wherein the second direction is a horizontal direction within an angle of about 45° with respect to the direction perpendicular to the direction of the force of gravity.

Arrangement 34: The device of any one of the above Arrangements, wherein the second direction is a horizontal direction substantially perpendicular to the direction of the force of gravity.

Arrangement 35: A diagnostic assay device for detecting an analyte in a sample specimen, the device comprising: a microreactor comprising a specimen-receiving chamber vertically above and fluidly connected to a reaction chamber comprising a porous wicking filter; and an absorbent strip pad that is in contact with the porous wicking filter, wherein the specimen-receiving chamber comprises an upper portion having a wide top opening, and a lower portion comprising a cylindrical cavity with a bottom opening adjacent to the reaction chamber, wherein the upper portion is wider than the lower portion and the bottom opening has a diameter narrower than the diameter of the cylindrical cavity, wherein the porous wicking filter is impregnated with a plurality of capture molecules adapted to specifically bind to the analyte and form an analyte-capture molecule complex and a plurality of detection molecules comprising a colorimetric component and adapted to specifically bind to the analyte-capture molecule complex, and wherein the porous wicking filter is oriented along a first axis and the absorbent strip pad is oriented along a second axis crossing the first axis.

Arrangement 36: The device of Arrangement 35, wherein the reaction chamber is oriented along a vertical axis and the absorbent strip pad is oriented along a horizontal axis.

Arrangement 37: The device of any of Arrangements 35-36, wherein the lower portion of the specimen-receiving chamber has a volume of 100-300 µl.

Arrangement 38: The device of any of Arrangements 35-37, wherein the absorbent strip pad is substantially free of capture molecules and detection molecules.

Arrangement 39: The device of any of Arrangements 35-38, wherein the absorbent strip pad comprises a test line, the test line comprising a plurality of binding molecules adapted to bind the analyte-capture molecule complex.

Arrangement 40: The device of any of Arrangements 35-39, wherein the microreactor is configured to receive a sample specimen containing the analyte and a buffer solution in the specimen-receiving chamber to form a sample solution and flow the sample solution in a first direction to contact the porous wicking filter in the reaction chamber and form therein the analyte-capture molecule complex, and to transfer the sample solution containing the analyte-capture molecule complex to the absorbent strip pad.

Arrangement 41: The device of Arrangement 40, wherein the absorbent strip pad is configured to flow therethrough, in a second direction crossing the first direction, the sample solution including the analyte-capture molecule complex and indicate a presence of the analyte-capture molecule complex.

Arrangement 42: A diagnostic assay kit for detecting an analyte in a sample specimen, the device comprising: a specimen collection unit configured for collecting a sample specimen containing the analyte; a diagnostic device comprising: a microreactor comprising a specimen-receiving chamber vertically above and fluidly connected to a reaction chamber, the reaction chamber having a cylindrical volume housing a porous wicking filter, the porous wicking filter comprising a plurality of capture molecules adapted to specifically bind to the analyte in the sample solution and form an analyte-capture molecule complex; and an absorbent strip pad that is in contact with the porous wicking filter; and a buffer solution, wherein the microreactor is configured to receive a sample specimen containing the analyte and a buffer solution in the specimen-receiving chamber to form a sample solution and flow the sample solution in a first direction to contact the porous wicking filter in the reaction chamber and form therein the analyte-capture molecule complex, and to transfer the sample solution containing the analyte-capture molecule complex to the absorbent strip pad, and wherein the absorbent strip pad is configured to flow therethrough, in a second direction crossing the first direction, the sample solution including the analyte-capture molecule complex and indicate a presence of the analyte-capture molecule complex.

Arrangement 43: The diagnostic assay kit of Arrangement 42, wherein the specimen collection unit comprises a swab configured to be wetted with the sample specimen.

Arrangement 44: The diagnostic assay kit of Arrangements 42 or 43, comprising a diagnostic device of any of Arrangements 1-41.

Arrangement 45: A method for identifying the presence of an analyte in a sample specimen, the method comprising: providing a device comprising: a microreactor comprising a specimen-receiving chamber vertically above and fluidly connected to a reaction chamber, the reaction chamber having a cylindrical volume and housing a porous wicking filter, the porous wicking filter comprising a plurality of capture molecules adapted to specifically bind to the analyte; and an absorbent strip pad that is in contact with the porous wicking filter, placing a sample specimen and a buffer solution in the specimen-receiving chamber to form a sample solution; flowing the sample solution through the microreactor in a first direction to contact the porous wicking filter in the reaction chamber and form therein an analyte-capture molecule complex; transferring the sample solution containing the analyte-capture molecule complex to the absorbent strip pad, such that the sample solution flows through the absorbent strip pad in a second direction crossing the first direction; and detecting the analyte-capture molecule complex in the absorbent strip pad to identify the presence of the analyte in the sample specimen.

Arrangement 46: The method of Arrangement 45, wherein the sample specimen is obtained from a human.

Arrangement 47: The method of Arrangement 45, wherein the sample specimen is obtained from an animal or a plant.

Arrangement 48: The method of Arrangement 45, wherein the sample specimen is obtained from a patient.

Arrangement 49: The method of Arrangement 48, wherein the patient is a human patient.

Arrangement 50: The method of any one of Arrangements 45-49, wherein the sample specimen comprises one or more of blood, urine, serum, plasma, saliva, cerebral spinal fluid, nasal secretions, pharyngeal secretions, urethral secretions and vaginal secretions.

Arrangement 51: The method of Arrangement 49, additionally comprising obtaining the sample specimen from the human patient using a swab.

Arrangement 52: The method of Arrangement 51, wherein obtaining the sample specimen comprises wetting a swab with the sample specimen.

Arrangement 53: The method of any one of Arrangements 43-52, wherein placing the sample specimen and a buffer solution in the specimen receiving chamber comprises inserting a swab comprising the sample specimen into the sample-receiving chamber.

Arrangement 54: The method of Arrangement 53, additionally comprising applying mechanical energy to the swab to cause the analyte to be extracted from the swab and mixed with the buffer solution.

Arrangement 55: The method of Arrangement 45, wherein the specimen-receiving chamber comprises an upper portion having a wide top opening adapted to receive a sample specimen comprising the analyte, and a lower portion comprising a cylindrical cavity and a bottom opening adjacent to the reaction chamber, wherein the upper portion is wider than the lower portion and the bottom opening has a diameter narrower than the diameter of the cylindrical cavity.

Arrangement 56: The method of Arrangement 55, wherein the lower portion of the specimen-receiving chamber stops and holds a swab inserted into the specimen-receiving region.

Arrangement 57: The method of Arrangement 55, wherein the specimen-receiving chamber has a funnel shape, and the lower portion is configured to hold a limited volume of the sample solution and the upper portion is configured to hold an excess volume of the sample solution in excess of the limited volume.

Arrangement 58: The method of any one of Arrangements 55-57, wherein the lower portion of the specimen-receiving chamber has a volume of 100-300 μl.

Arrangement 59: The method of any one of Arrangements 45-58, wherein the sample solution is transferred to the absorbent strip pad in part using gravity.

Arrangement 60: The method of any one of Arrangements 45-59, wherein the sample solution is transferred from the specimen-receiving region to the absorbent strip pad in part by capillary action in addition to gravity.

Arrangement 61: The method of any one of Arrangements 45-60, wherein the porous wicking filter contacts the sample solution at an upper end thereof and contacts the absorbent strip pad at a lower end thereof.

Arrangement 62: The method of any one of Arrangements 45-61, wherein the porous wicking filter additionally comprises a plurality of detection molecules comprising a colorimetric component and adapted to specifically bind to the analyte and/or the analyte-capture molecule complex.

Arrangement 63: The method of Arrangement 62, wherein the porous wicking filter comprises detection molecules at a concentration of about 0.001 to 0.1% in the sample solution.

Arrangement 64: The method of Arrangement 62, wherein the colorimetric component is a dye.

Arrangement 65: The method of Arrangement 62, wherein the colorimetric component is one or more of a cellulose nano bead, colloidal gold, a gold nano shell or a latex bead.

Arrangement 66: The method of any one of Arrangements 45-65, wherein the absorbent strip pad receives the sample solution from the reaction chamber and transfers the sample solution in a lateral direction to cause a visual indication of a presence of the analyte-capture molecule complex.

Arrangement 67: The method of any one of Arrangements 45-66, wherein the absorbent strip pad comprises a test line, the test line comprising a plurality of binding molecules adapted to bind the analyte-capture molecule complex.

Arrangement 68: The method of Arrangement 67, wherein detecting the analyte-capture molecule complex in the absorbent strip pad comprises visualizing bound analyte-capture molecule complexes at the test line.

Arrangement 69: The method of any one of Arrangements 45-68, wherein the porous wicking filter comprises a porous polymeric material.

Arrangement 70: The method of any one of Arrangements 45-69, wherein the porous wicking filter is impregnated with the capture molecule prior to forming the sample solution.

Arrangement 71: The method of any one of Arrangements 45-70, wherein the porous wicking filter comprises capture molecules at a concentration of 0.1 to 2 mg/ml in the sample solution.

Arrangement 72: The method of any of Arrangements 45-71, wherein the absorbent strip pad transfers the sample solution in the second direction substantially by capillary action.

Arrangement 73: The method of any of Arrangements 45-72, wherein the absorbent strip pad is substantially free of the capture molecules prior to forming the sample solution.

Arrangement 74: The method of any one of Arrangements 62-73, wherein the absorbent strip pad is substantially free of the detection molecules prior to forming the sample solution.

Arrangement 75: The method of any one of Arrangements 45-74, wherein the capture molecule is an antibody.

Arrangement 76: The method of any one of Arrangements 45-75, wherein the analyte is an antigen.

Arrangement 77: The method of Arrangement 76, wherein the antigen is a SARS-CoV-2, RSV, influenza A or influenza B antigen.

Arrangement 78: The method of Arrangement 77, wherein the capture molecule is a SARS-CoV-2, RSV, influenza A or influenza B antibody.

Arrangement 79: The method of any one of Arrangements 45-78, wherein the first direction is a vertical direction within an angle of about 45° with respect to the direction of the direction of the force of gravity.

Arrangement 80: The method of any of Arrangements 45-79, wherein the first direction is a vertical direction substantially parallel to a direction of the force of gravity.

Arrangement 81: The method of any one of Arrangements 45-80, wherein the second direction is a horizontal direction within an angle of about 45° with respect to the direction perpendicular to the direction of the force of gravity.

Arrangement 82: The method of any one of Arrangements 45-81, wherein the second direction is a horizontal direction substantially perpendicular to the direction of the force of gravity.

Arrangement 83: A method for identifying the presence of an analyte in a sample specimen, the method comprising: providing a device comprising: a microreactor comprising a specimen-receiving chamber vertically above and fluidly connected to a reaction chamber, the reaction chamber housing a porous wicking filter impregnated with a plurality of capture molecules adapted to specifically bind to the analyte and form an analyte-capture molecule complex and a plurality of detection molecules comprising a colorimetric component and adapted to specifically bind to the analyte-capture molecule complex; and an absorbent strip pad that is in contact with the porous wicking filter and that comprises a test line, wherein the test line comprises a plurality of binding molecules adapted to bind the analyte-capture molecule complex; placing a sample specimen and a buffer solution in the specimen-receiving chamber to form a sample solution; and visualizing the analyte-capture molecule complex bound at the test line to identify the presence of the analyte in the sample specimen, wherein the sample solution flows through the microreactor in a first direction to contact the porous wicking filter in the reaction chamber and form therein an analyte-capture molecule complex, wherein the first direction is a vertical direction within an angle of about 45° with respect to the direction of the direction of the force of gravity, and wherein the sample solution containing the analyte-capture molecule complex is transferred to the absorbent strip pad, such that the sample solution flows through the absorbent strip pad in a second direction crossing the first direction and analyte-detection molecule complex is bound at the test line, wherein the second direction is a horizontal direction within an angle of about 45° with respect to the direction perpendicular to the direction of the force of gravity.

Arrangement 84: The method of Arrangement 83, wherein the sample solution has a volume of 100-350 μl.

Arrangement 85: The method of any of Arrangements 83-84, wherein the porous wicking filter has a capacity of about 100 μl.

Arrangement 86: The method of any of Arrangements 83-85, wherein the specimen-receiving chamber comprises an upper portion having a wide top opening adapted to receive the sample specimen comprising the analyte, and a lower portion comprising a cylindrical cavity having a volume of about 100-300 μl.

Arrangement 87: The method of any one of Arrangements 83-86, wherein the absorbent strip pad receives the sample solution from the reaction chamber and transfers the sample solution in a lateral direction to cause a visual indication of a presence of the analyte-capture molecule complex.

Unless the context clearly requires otherwise, throughout the description and the claims, the words "comprise," "comprising," "include," "including" and the like are to be construed in an inclusive sense, as opposed to an exclusive or exhaustive sense; that is to say, in the sense of "including, but not limited to." The word "coupled," as generally used herein, refers to two or more elements that may be either directly connected, or connected by way of one or more intermediate elements. Likewise, the word "connected," as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number, respectively. The word "or" in reference to a list of two or more items, that word covers all of the following interpretations of the word: any of the items in the list, all of the items in the list, and any combination of the items in the list.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or whether these features, elements and/or states are included or are to be performed in any particular embodiment.

While certain embodiments have been described, these embodiments have been presented by way of example only and are not intended to limit the scope of the disclosure. Indeed, the novel apparatus, methods, and systems described herein may be embodied in a variety of other forms; furthermore, various omissions, substitutions and changes in the form of the methods and systems described herein may be made without departing from the spirit of the disclosure. For example, while features are presented in a given arrangement, alternative embodiments may perform similar functionalities with different components and/or sensor topologies, and some features may be deleted, moved, added, subdivided, combined, and/or modified. Each of these features may be implemented in a variety of different ways. Any suitable combination of the elements and acts of the various embodiments described above can be combined to provide further embodiments. The various features and processes described above may be implemented independently of one another or may be combined in various ways. All possible combinations and subcombinations of features of this disclosure are intended to fall within the scope of this disclosure.

What is claimed is:

1. A diagnostic assay device for detecting an analyte in a sample specimen, the device comprising:
   a microreactor comprising a specimen-receiving chamber vertically above and fluidly connected to a reaction chamber, the reaction chamber having a cylindrical volume housing a porous wicking filter, the porous wicking filter comprising a plurality of capture molecules adapted to specifically bind to the analyte in the sample solution and form an analyte-capture molecule complex; and
   an absorbent strip pad that is in contact with the porous wicking filter,
   wherein the specimen-receiving chamber comprises an upper portion and a lower portion, the upper portion having a top opening adapted to receive a swab having the sample specimen collected thereon and a buffer solution, and the lower portion having a cavity configured to immerse at least a tip portion of the swab in the buffer solution to extract the sample specimen from the tip portion of the swab to form a sample solution initially having an analyte concentration in the cavity adjacent to the porous wicking filter that is higher relative to an analyte concentration in the upper portion immediately after extracting the sample specimen from the tip portion of the swab,
   the microreactor further configured to flow the sample solution in a first direction to contact the porous wicking filter in the reaction chamber and form therein the analyte-capture molecule complex, and to transfer the sample solution containing the analyte-capture molecule complex to the absorbent strip pad,
   wherein the dimensions and microstructure of the porous wicking filter are such that the porous wicking filter is configured to hold a volume of the sample solution that is about equal to or less than a volume of the sample solution held by the cavity, and
   wherein the absorbent strip pad is configured to flow therethrough, in a second direction crossing the first direction, the sample solution including the analyte-capture molecule complex and indicate a presence of the analyte-capture molecule complex.

2. The device of claim 1, wherein the cavity in the lower portion of the specimen-receiving chamber is cylindrical and the lower portion of the specimen-receiving chamber additionally comprises a bottom opening adjacent to the reaction chamber, and wherein the upper portion of the specimen-receiving chamber is wider than the lower portion and the bottom opening has a diameter narrower than the diameter of the cylindrical cavity.

3. The device of claim 2, wherein the upper portion of the specimen-receiving chamber is configured to hold an excess volume of the sample solution held by the cylindrical cavity in the lower portion of the specimen-receiving chamber.

4. The device of claim 1, wherein the lower portion of the specimen-receiving chamber has a volume of 100-300 µl.

5. The device of claim 1, wherein the lower portion of the specimen-receiving chamber is configured to stop and hold the swab inserted into the specimen-receiving region.

6. The device of claim 1, wherein the porous wicking filter is configured to contact the sample solution at an upper end thereof and contacts the absorbent strip pad at a lower end thereof.

7. The device of claim 1, wherein the porous wicking filter additionally comprises a plurality of detection molecules comprising a colorimetric component and adapted to specifically bind to the analyte and/or the analyte-capture molecule complex.

8. The device of claim 7, wherein the colorimetric component is one or more of a dye, a cellulose nano bead, colloidal gold, a gold nano shell or a latex bead.

9. The device of claim 7, wherein the absorbent strip pad is substantially free of the detection molecules.

10. The device of claim 1, wherein the absorbent strip pad comprises a test line, the test line comprising a plurality of binding molecules adapted to bind the analyte-capture molecule complex.

11. The device of claim 1, wherein the porous wicking filter comprises an elongated portion in which an upper portion proximal to the specimen-receiving chamber has a higher concentration of one or both of the capture molecules and detection molecules relative to a lower portion proximal to the absorbent strip pad.

12. The device of claim 1, wherein the porous wicking filter comprises a porous polymeric material.

13. The device of claim 12, wherein the porous wicking filter comprises an irregular structure of fibers with a packing density of about 0.35 g/cc.

14. The device of claim 1, wherein the absorbent strip pad is configured to transfer the sample solution in the second direction substantially by capillary action.

15. The device of claim 1, wherein the absorbent strip pad is substantially free of the capture molecules.

16. The device of claim 1, wherein the porous wicking filter has dimensions and porosity configured for a controlled flow rate, such that a time duration corresponding to the passage of the sample solution through the reaction chamber corresponds to a reaction time for substantial formation of the analyte-capture molecule complex.

17. The device of claim 1, wherein the analyte is an antigen and the capture molecule comprises an antibody or portion thereof.

18. The device of claim 17, wherein the antigen is a SARS-CoV-2, RSV, influenza A or influenza B antigen.

19. The device of claim 1, wherein the first direction is a vertical direction within an angle of about 45° with respect to the direction of the direction of the force of gravity.

20. The device of claim 1, wherein the second direction is a horizontal direction within an angle of about 45° with respect to the direction perpendicular to the direction of the force of gravity.

21. A diagnostic assay device for detecting an analyte in a sample specimen, the device comprising:
   a microreactor comprising a specimen-receiving chamber vertically above and fluidly connected to a reaction chamber comprising a porous wicking filter; and
   an absorbent strip pad that is in contact with the porous wicking filter,
   wherein the specimen-receiving chamber comprises an upper portion having a wide top opening adapted to receive a swab having the sample specimen collected thereon and a buffer solution, and a lower portion comprising a cylindrical cavity with a bottom opening adjacent to the reaction chamber, the lower portion configured to immerse at least a tip portion of the swab in the buffer solution to extract the sample specimen from the tip portion of the swab to form a sample solution initially having an analyte concentration in the cavity adjacent to the porous wicking filter that is higher relative to an analyte concentration in the upper portion immediately after extracting the sample specimen from the tip portion of the swab,
   wherein the upper portion is wider than the lower portion and the bottom opening has a diameter narrower than the diameter of the cylindrical cavity,
   wherein the dimensions and microstructure of the porous wicking filter are such that the porous wicking filter can hold a volume of the sample solution that is about equal to or less than a volume of the sample solution held by the cavity,
   wherein the porous wicking filter is impregnated with a plurality of capture molecules adapted to specifically bind to the analyte and form an analyte-capture molecule complex and a plurality of detection molecules comprising a colorimetric component and adapted to specifically bind to the analyte-capture molecule complex, and wherein the porous wicking filter is oriented along a first axis and the absorbent strip pad is oriented along a second axis crossing the first axis.

22. The device of claim 21, wherein the reaction chamber is oriented along a vertical axis and the absorbent strip pad is oriented along a horizontal axis.

23. The device of claim 21, wherein the lower portion of the specimen- receiving chamber has a volume of 100-300 μl.

24. The device of claim 21, wherein the absorbent strip pad is substantially free of capture molecules and detection molecules.

25. The device of claim 21, wherein the absorbent strip pad comprises a test line, the test line comprising a plurality of binding molecules adapted to bind the analyte-capture molecule complex.

26. The device of claim 21, wherein the microreactor is configured to flow the sample solution in a first direction to contact the porous wicking filter in the reaction chamber and form therein the analyte-capture molecule complex, and to transfer the sample solution containing the analyte-capture molecule complex to the absorbent strip pad.

27. The device of claim 26, wherein the absorbent strip pad is configured to flow therethrough, in a second direction crossing the first direction, the sample solution including the analyte-capture molecule complex and indicate a presence of the analyte-capture molecule complex.

\* \* \* \* \*